(12) United States Patent
Kurogama et al.

(10) Patent No.: US 6,637,656 B2
(45) Date of Patent: Oct. 28, 2003

(54) OPTICAL READING APPARATUS AND OPTICAL READING METHOD

(75) Inventors: Tatsuji Kurogama, Hachioji (JP); Makoto Banno, Hachioji (JP); Nobuyuki Baba, Hachioji (JP)

(73) Assignee: Konica Corporation, Tokyo (JP)

( * ) Notice: Subject to any disclaimer, the term of this patent is extended or adjusted under 35 U.S.C. 154(b) by 129 days.

(21) Appl. No.: 09/878,430

(22) Filed: Jun. 12, 2001

(65) Prior Publication Data

US 2001/0050313 A1 Dec. 13, 2001

(30) Foreign Application Priority Data

Jun. 13, 2000 (JP) .................................... 2000-176599

(51) Int. Cl.[7] ................................................ G06K 7/10
(52) U.S. Cl. ........................ 235/462.25; 235/462.27; 235/454; 235/472.01
(58) Field of Search ........................ 235/462.25, 462.27, 235/472.01, 454

(56) References Cited

U.S. PATENT DOCUMENTS

| | | | | |
|---|---|---|---|---|
| 3,745,354 A | * | 7/1973 | Vargo | 235/462.02 |
| 6,098,883 A | * | 8/2000 | Zocca et al. | 235/462.27 |
| 6,102,291 A | * | 8/2000 | Mazzone | 235/462.01 |
| 6,325,289 B1 | * | 12/2001 | Mazzone | 235/462.14 |
| 6,435,412 B2 | * | 8/2002 | Tsi et al. | 235/462.41 |

* cited by examiner

Primary Examiner—Michael G. Lee
Assistant Examiner—Allyson Sanders
(74) Attorney, Agent, or Firm—Finnegan, Henderson, Farabow, Garrett & Dunner, L.L.P.

(57) ABSTRACT

The present invention concerns an optical reading apparatus and an optical reading method for obtaining objective information by reading a subject and processing the read information through an arithmetic processing. The optical reading apparatus includes a light source to irradiate a light flux onto a subject; a photo-receiving element to receive a reflected light or a transmitted light of the light flux irradiated onto the subject, and to generate signals based on an opt-electronic converting action; an arithmetic processing section to apply an arithmetic processing to the signals, in order to detect information of the subject; and a calculating section to apply a calculating processing, for reducing noise components caused by optical factors, to the signals generated by the photo-receiving element, in order to obtain output signals in which noise components are reduced, before the arithmetic processing section applies the arithmetic processing to the signals.

17 Claims, 23 Drawing Sheets

PORTION AT WHICH
ECLIPSE OCCURS $I_1 < I_2$ $I_1 > I_2$

OPTICAL READING APPARATUS AND OPTICAL READING METHOD

BACKGROUND OF THE INVENTION

The present invention relates to methods and apparatus for optically reading information, and specifically relates to an optical reading apparatus and an optical reading method for obtaining objective information by reading a subject and processing the read information through an arithmetic processing.

Conventionally, when deriving the objective information from optical information read optically, the objective information is detected or recognized by applying a processing-operation, such as an image-analyzing operation, etc., to signals obtained by reading the optical information. For instance, the barcode recognition, the character recognition, the shape recognition, etc. are included in the above operation.

Specifically, noise components caused by an optical mechanism are included in opt-electronic conversion results outputted by the optical reading apparatus, which comprises a light source, a photo-receiving element and a calculating means, and irradiates a light bundle emitted from the light source onto the subject, and opt-electronically converts its reflected light or its transmitted light with the photo-receiving element, and then, detects the information of the subject by applying the an arithmetic processing to the signals converted opt-electronically.

For instance, in case that different kinds of printed patterns or the like exist on the surface of the subject when the light bundle emitted from the light source is irradiated onto the subject to detect a concave or a convex of the surface of the subject with its reflected light, the signals opt-electronically converted by the photo-receiving element include noise components, caused by an optical mechanism, which is overlapped with the concave or convex information as a detecting subject.

As mentioned above, when noise components caused by optical factors is larger than the opt-electronically converted signals, etc., and, for instance, characters and numerals formed in either the convex or the concave are detected/recognized by detecting the aforementioned convex or concave formed on the surface of the subject, and various kinds of patterns printed or residing on the surface of the subject works as noise components caused by optical factors, such the noise components considerably impede an accurate reading action for the information, which include deviations of the convex or the concave as a detecting object.

Incidentally, explaining according to the aforementioned example, in case that the information, being a detecting object of the subject, is at least one of the convex or the concave formed on the surface of the subject, and the noise components caused by optical factors, such as the distribution of reflecting rates or the distribution of transmitting rates, exist on the surface of the subject, when detecting them with a reflected light or a transmitting light, the noise components, caused by such as colors and density patterns, etc., which influences to the reflecting rate or the transmitting rate on the surface of the subject, are integrated with the detected signals including the information of the convex or the concave being the detecting object.

Accordingly, in case that the noise components are the optical information caused by optical factors, when optically reading the information being the detecting object, it has been very difficult to separate both of them or to remove only the noise components from the detected signals.

Conventionally, methods for eliminating fine noises caused by electronic factors or noises, having a frequency of 50–60 Hz and generated by a fluorescent lamp, have been well known. Further, although, other than the above methods, a method for discriminating figures and characters by applying an arithmetic filtering processing to two-dimensional information (image data) thereafter, when the noise components, overlapping with the signals itself generated by the photo-receiving element, are large, it is impossible to accurately detect/recognize the information being a objective detecting object, even if the CPU in the later stage applies an arithmetic processing for its image analysis.

SUMMARY OF THE INVENTION

The present invention is attained in view of the above-mentioned problems in conventional optical reading apparatus and optical reading methods. In a method and an apparatus, in which objective information are obtained by optically reading the subject and applying arithmetic processing, it is an object of the present invention to reduce the influence of the noise components caused by optical factors and to improve the accuracy of the necessary information being a detecting object.

Accordingly, to overcome the cited shortcomings, the abovementioned object of the present invention can be attained by optical reading apparatus and methods described as follow.

(1) An optical reading apparatus, comprising: a light source to irradiate a light flux onto a subject; a photo-receiving element to receive a reflected light or a transmitted light of the light flux irradiated onto the subject, and to generate signals based on an opt-electronic converting action; an arithmetic processing section to apply an arithmetic processing to the signals, in order to detect information of the subject; and a calculating section to apply a calculating processing, for reducing noise components caused by optical factors, to the signals generated by the photo-receiving element, in order to obtain output signals in which noise components are reduced, before the arithmetic processing section applies the arithmetic processing to the signals.

(2) The optical reading apparatus of item 1, wherein the photo-receiving element is capable of detecting a photo-receiving position, and the optical reading apparatus detects a distribution of deviations of at least one of a convex or a concave on the subject, based on the variation of the photo-receiving position.

(3) The optical reading apparatus of item 2, wherein the noise components caused by optical factors, arises from a distribution of light-reflecting rates or light-transmitting rates of the subject.

(4) The optical reading apparatus of item 3, wherein the calculating section finds a first centroid of the light on the photo-receiving element, and a second centroid of the light on the photo-receiving element, caused by the distribution of light-reflecting rates or light-transmitting rates of the subject, from the signals generated by the photo-receiving element, and the output signals, in which the noise components are reduced, are obtained by applying the calculating processing, for reducing the noise components caused by optical factors, to the signals generated by the photo-receiving element by subtracting the second centroid of the light from the first centroid of the light.

(5) The optical reading apparatus of item 4, wherein the calculating section finds the second centroid of the light from a total quantity of the light on the photo-receiving element.

(6) The optical reading apparatus of item 5, wherein the photo-receiving element is a one-dimensional PSD (Position Sensitive Detector), and the calculating section finds the first centroid of the light from two electronic current values or two voltage values outputted from both ends of the one-dimensional PSD, and the calculating section finds the second centroid of the light from a sum of two electronic current values or two voltage values outputted from both ends of the one-dimensional PSD.

(7) The optical reading apparatus of item 6, wherein the calculating section comprises a memory to store the two electronic current values or the two voltage values outputted from the both ends of the one-dimensional PSD, and the calculating section finds the first centroid of the light from two electronic current values or two voltage values stored in the memory, and the memory also stores the sum of the two electronic current values or the two voltage values, and the calculating section finds the second centroid of the light from the sum stored in the memory.

(8) The optical reading apparatus of item 6, wherein the light flux is irradiated onto the subject while the subject is moving relative to the light flux, and the light flux has a width in a moving direction of the subject or the light flux, and the light on the photo-receiving element has a light-spot width corresponding to the width of the light flux, and the calculating section finds the second centroid of the light from the sum of two electronic current values or two voltage values outputted from the both ends of the one-dimensional PSD, in respect to the light-spot width.

(9) The optical reading apparatus of item 1, wherein the light flux is irradiated onto the subject while the subject is moving relative to the light flux in a moving direction, and the light flux is a linear light being slender in a direction orthogonal to the moving direction.

(10) The optical reading apparatus of item 3, wherein the calculating section finds the noise components caused by optical factors, based on a difference between frequency components of the signals generated by the photo-receiving element.

(11) The optical reading apparatus of item 1, wherein the photo-receiving element is either a PSD, a PD (Photo Diode) or a solid-state imager.

(12) The optical reading apparatus of item 1, wherein the optical reading apparatus detects a distribution of deviations of at least one of a convex or a concave formed on the subject, and the photo-receiving element is a multi-segmented photo-diode, and either a knife edge method, an astigmatism method or a beam-size method is employed for detecting the distribution of deviations of at least one of a convex or a concave formed on the subject.

(13) The optical reading apparatus of item 1, further comprising: an aperture to optically shade the noise components caused by optical factors.

(14) The optical reading apparatus of item 1, wherein a plurality of light sources, each of which is equivalent to the light source, are symmetrically disposed to optically reduce the noise components caused by optical factors.

(15) The optical reading apparatus of item 1, wherein a plurality of photo-receiving elements, each of which is equivalent to the photo-receiving element, are symmetrically disposed, and photo-receiving results outputted from the photo-receiving elements are synthesized or selected to optically reduce the noise components caused by optical factors.

(16) A method for reading optical information, comprising the steps of: irradiating a light flux onto a subject; receiving a reflected light or a transmitted light of the light flux, irradiated onto the subject, with a photo-receiving element; generating signals based on an opt-electronic converting action performed by the photo-receiving element; applying a calculating processing, for reducing noise components caused by optical factors, to the signals, in order to obtain output signals in which noise components are reduced; and applying an arithmetic processing to the output signals, in order to detect information of the subject.

(17) The method of item 16, wherein it is possible to detect a photo-receiving position on the photo-receiving element from the signal, and a distribution of deviations of at least one of a convex or a concave on the subject is detected, based on the variation of the photo-receiving position.

(18) The method of item 17, wherein the noise components caused by optical factors, arises from a distribution of light-reflecting rates or light-transmitting rates of the subject.

(19) The method of item 18, wherein a first centroid of the light on the photo-receiving element, and a second centroid of the light on the photo-receiving element, caused by the distribution of light-reflecting rates or light-transmitting rates of the subject, are found from the signals generated by the photo-receiving element, and the output signals, in which the noise components are reduced, are obtained by applying the calculating processing, for reducing the noise components caused by optical factors, to the signals generated by the photo-receiving element by subtracting the second centroid of the light from the first centroid of the light.

(20) The method of item 19, wherein the second centroid of the light is found from a total quantity of the light on the photo-receiving element.

Further, to overcome the abovementioned problems, other optical reading apparatus and optical reading methods, embodied in the present invention, will be described as follow:

(21) An optical reading method, characterized in that,
in the optical reading method, in which a light source, a photo-receiving element and an arithmetic processing section are included, and information of a subject are detected by opt-electronically converting a reflected light or a transmitted light of the light bundle emitted from the light source in respect to the subject having optical information and by applying an arithmetic processing to opt-electronically converted results,
noise components, caused by optical factors when the photo-receiving element detects the reflected light or the transmitted light of the light bundle emitted from the light source, are reduced by performing an elimination calculating processing as a separate arithmetic processing to be performed before the arithmetic processing.

(22) An optical reading apparatus, characterized in that,
in the optical reading apparatus, which comprises a light source, a photo-receiving element and an arithmetic processing section, and detects information of a subject by opt-electronically converting a reflected light or a transmitted light of the light bundle emitted from the light source in respect to the subject having optical information and by applying an arithmetic processing to opt-electronically converted results, the optical reading apparatus comprises an elimination calculating section for performing an elimination calculating processing as a separate arithmetic processing to be performed before the arithmetic processing to reduce noise components caused by optical factors when the photo-receiving element detects the reflected light or the transmitted light of the light bundle emitted from the light source.

For instance, to discriminate and classify papers based on a reflecting rate of each paper in a factory, etc., in which box-type products made of papers are handled, the intensity of the light reflected from the paper, being an inspection subject, could be measured to discriminate and classify papers. The measurement is performed under a room lamp, a fluorescent lamp in the vicinity or an illuminating light source provided with the photo-receiving element, and the signals outputted from the photo-receiving element are analogue-to-digital converted to store them. In this case, when a shadow portion of a box arrives at the detecting position, the intensity of the received light abruptly decreases at the shadow portion, and it is erroneously determined that the box has a very low reflecting rate. To avoid the above drawback, the information lower than a predetermined light intensity is eliminated by performing logical judgments. Thus, it becomes possible to accurately discriminate the subject.

Accordingly, in the optical reading apparatus of item 22, the optical reading apparatus comprises at least a photo-receiving element, and opt-electronically converts the received light in such a manner that the light reflected from the subject enters into the photo-receiving element under the room lamp, etc., and applies processing, equivalent to mathematic logical calculations, such as a differential calculus, an integral calculus, sum and subtract calculus, etc., to the signals generated by the photo-receiving element or the analogue-to-digital converted and/or amplified signals to find noise components caused by optical factors with simpler arithmetic elements and circuits, and then, obtains the optimum signals by subtracting the noise components, etc.

In other words, the noise components are removed from the original signals being detecting signals at the initial stage, and a binary coding processing is applied to the obtained signals to perform image processing.

(23) The optical reading apparatus cited in item 22, characterized in that the elimination calculating section analogue-to-digital converts photo-electronically converted results to store digital data into a memory, and finds the noise components caused by optical factors from the digital data stored in the memory to reduce the noise components included in the digital data.

For instance, to discriminate and classify papers based on a reflecting rate of each paper, the intensity of the light reflected from the paper, being an inspection subject, could be measured to discriminate and classify papers, as mentioned in regard to items 21–22. In this case, the signals outputted from the photo-receiving element are analogue-to-digital converted to store digital data into a memory, and the arithmetic processing is performed in respect to the data stored in the memory by executing software. As mentioned above, when a plurality of data are stored in the memory and utilized for the arithmetic processing, it becomes possible to analyze a plurality of data with various kinds of method to retrieve many information, and to improve the accuracy of lowering the noise components. Specifically, sometimes, it becomes possible to eliminate noise components, which cannot be separated by means of mechanical methods, by performing complicated arithmetic processing.

In the above simplified example, when the shadow portion arrives at the detecting position, the intensity of the received light abruptly decreases, and therefore, it is erroneously determined that the subject has a very low reflecting rate. To avoid the above drawback, the data lower than a predetermined light intensity is reduced from the stored data at the initial stage of the arithmetic processing by performing logical judgments. In this method, the signals are initially processed to obtain the signals in which the noise components are reduced, namely, the noise components are initially removed from the original signals by calculating with data stored in the memory. Accordingly, since the signals, from which noise components are already removed, are encoded into binary or multivalued data to conduct the image processing, it is possible to precisely detect the information under the detecting operation, and further, the abovementioned method is superior to conventional methods for discriminating a shape or letters by afterwardly applying an arithmetic filtering processing to two-dimensional information stored in advance.

Further, as a concrete example of the configuration, there will be exemplified the apparatus, in which the photo-receiving element is a position detecting element such as a PSD or the like being detectable of the centroid of the received light, and the light source is a Laser Diode (hereinafter referred to as a LD), and the irradiation light is a linear light obtained by shaping the light bundle emitted from the light source, with a cylindrical lens, etc., and the subject is a card-type subject, which moves at a constant velocity and comprises at least one of a concave and a convex. When detecting the convex or the concave in the above situation and the PSD, serving as a photo-receiving element, is apart from the subject, since the light emitted from the light source is a coherent light, a large amount of Fresnel diffraction would occur at, for instance, edges of optical members, such as a supporting member of the optical system, an aperture member, etc., which would shade the optical path. This Fresnel diffraction generates noise components, which disturbs the distribution of incident light entering into the PSD, etc. More accurate measurements can be achieved by finding Fresnel diffraction components from the length of the optical path and the distribution of luminous intensity, etc., and finding the noise components onto the PSD, caused by the Fresnel diffraction components, and applying the arithmetic processing to the signals detected by the PSD so as to reduce the noise components.

Incidentally, the Fresnel diffraction possibly occurs, even when the subject is transparent. For instance, when it is intended to accurately reading positions of characters or symbols formed on transparent subject 102, as shown in FIG. 23, a large amount of Fresnel diffraction are generated by shaping the light bundle emitted from LD 9 to irradiate the shaped light onto transparent subject 102, and impede an accurate operation for reading the positions of small characters or symbols. Accordingly, the Fresnel diffraction components, which is a function of distance L between the subject and PD array 104, are calculated from the signals outputted by PD array 104 (or the CCD sensor or the PSD), and accurate information can be obtained by subtracting the calculated Fresnel diffraction components from the output signals of PD array 104.

(24) The optical reading apparatus cited in item 22 or item 23, characterized in that, the information of the subject, being a detecting object, is information in respect to at least one of the concave and the convex on the surface, and the noise components caused by the optical factors arise from the distribution of light-reflecting rates or the distribution of light-transmitting rates.

Incidentally, when the information of the subject, being a detecting object, is information in respect to at least one of the concave and the convex on the surface, and the noise components caused by the optical factors arise from the distribution of reflecting rates or the distribution of transmitting rates due to the density variation on the surface of the subject (a pattern having color contrast, a pattern having different colors, such as black and white, etc., etc.), it is difficult to discriminate between the optical information detected from at least one of the concave and the convex on the surface of the subject and the optical information detected from the density variation on the surface of the subject. However, the accuracy of the necessary information, being a detecting object, can be improved by performing the elimination calculating processing in the configuration of item 21 or item 22 before performing the arithmetic processing to reduce the influence of the noise components caused by optical factors.

(25) The optical reading apparatus cited in any one of items 22–24, characterized in that, the noise components caused by optical factors are detected based on differences between frequency components of the photo-electronically converted results.

Incidentally, when the information of the subject, being a detecting object, is information in respect to at least one of the concave and the convex on the surface, and the noise components caused by the optical factors arise from the distribution of reflecting rates or the distribution of transmitting rates due to the density variation on the surface of the subject, it is difficult to discriminate between the optical information detected from at least one of the concave and the convex on the surface of the subject and the optical information detected from the density variation on the surface of the subject. Further, the noise components emerge in response to the width pitch of the pattern and sometimes indicate movements, which would be resolved into the frequency domain, such as strengthening or weakening, etc. Accordingly, the accuracy of the necessary information, being a detecting object, can be improved by detecting the noise components based on the differences between frequency components of the optical information when performing the elimination calculating processing in the configuration of item 21 or item 22 before performing the arithmetic processing to reduce the influence of the noise components caused by optical factors.

(26) An optical reading method, characterized in that,
in the optical reading method, in which a distribution of deviations of at least one of a convex or a concave, recorded on a subject, is detected by the steps of irradiating a light bundle emitted from a light source onto the surface of the subject, guiding the light reflected from the surface of the subject to a photo-receiving element being capable of detecting a receiving position of the reflected light, and applying an arithmetic processing, for finding a centroid of the reflected light, to the signals photo-electronically converted by the photo-receiving element,
the distribution of deviations of at least one of the convex or the concave, recorded on the subject, is detected by the steps of finding the centroid of the reflected light caused by a distribution of reflecting rates of the subject, and subtracting the centroid of the reflected light caused by a distribution of reflecting rates of the subject from the centroid of the reflected light found from the signals photo-electronically converted by the photo-receiving element.

(27) An optical reading apparatus, characterized in that,
in the optical reading apparatus, in which a distribution of deviations of at least one of a convex or a concave, recorded on a subject, is detected by the steps of irradiating a light bundle emitted from a light source onto the surface of the subject, guiding the light reflected from the surface of the subject to a photo-receiving element being capable of detecting a receiving position of the reflected light, and applying an arithmetic processing, for finding a centroid of the reflected light, to the signals photo-electronically converted by the photo-receiving element,
the distribution of deviations of at least one of the convex or the concave, recorded on the subject, is detected by the steps of finding the centroid of the reflected light caused by a distribution of reflecting rates of the subject, and subtracting the centroid of the reflected light caused by a distribution of reflecting rates of the subject from the centroid of the reflected light found from the signals photo-electronically converted by the photo-receiving element.

Generally speaking, in the operation for optically reading the information with the reflected light, the variation of reflecting rates on the surface of the subject caused by the information, being different from the information of the detecting object, could be the cause of a big confusion in respect to the information of the detecting object. Specifically, when other signals (quasi-signals), the amplitude of which is equivalent to or larger than that of the original signals to be obtained, is outputted from the photo-receiving element in a state of overlapping each other, it is virtually impossible to eliminate the quasi-signals in advance only by its mechanism and/or optical configuration. It becomes possible, however, to reduce the noise components, disturbing as the quasi-signals, by performing the steps of storing the signals outputted from the photo-receiving element into a memory, deriving the information in regard to the variation of reflecting rates on the surface of the subject in an arithmetic processing operation, and removing the information from the signals outputted from the photo-receiving element. Incidentally, the arithmetic processing operation, performed in this case, is a kind of simulation calculating operation.

An apparatus, in which the photo-receiving element is a position detecting element, such as the PSD, etc., being capable of detecting the centroid of the received light, the light source is the LD (Laser Diode), the illumination light is a linear light formed by shaping the light bundle emitted from the light source with a cylindrical lens, etc., the subject is a card-type subject, which moves at a constant velocity and comprises at least one of a concave and a convex, and the PSD can receive the linear light corresponding to the convex or the concave projected on the PSD, is assumed as a concrete example. Incidentally, when a one-dimensional PSD is employed for the PSD serving as a photo-receiving element, two electronic currents can be outputted from the both ends of the photo-receiving element. In this case, it is possible to derive the centroid position of the light received on the PSD from the arithmetic processing of the value, obtained through the processes of the I/V conversion, the amplifying operation and the A/D conversion of the two electronic currents. Further, by image-processing the information of the centroid position by means of a processing device such as a computer, etc., and recognizing the information as the convex or the concave, it is possible to distinguish the information of characters, numerals, etc. formed in either the convex or the concave by embossing the subject.

In other words, it is possible to obtain the accurate optical information of at least one of the convex or the concave, in which the noise components are reduced, by calculating the centroid position of the light in respect to the noise components, serving as quasi-signals, from the optical information in proportion to the distribution of reflecting rates, and by subtracting the centroid position of the light in respect to the noise components from the information of the centroid position of the light, which is initially found from the light received on the PSD by directly applying the arithmetic processing.

(28) The optical reading apparatus cited in item 27, characterized in that, the photo-receiving element is either a PSD, a PD (Photo Diode) or a solid-state imager.

In the abovementioned optical reading apparatus, the outputs of the photo-receiving element in a time passage domain are in proportion to the distribution of reflecting rates of the subject, and it is possible to conduct the aforementioned subtracting operation based on the information of the outputs of the photo-receiving element stored within a short time. Therefore, it becomes possible to complete the arithmetic processing more quickly than in the method of finding the distribution after storing all of the information in the memory.

(29) The optical reading apparatus cited in item 24 or item 25, characterized in that, the information is detected by employing a multi-segmented photo-diode for the photo-receiving element and by applying any one of a knife edge method, an astigmatism method, a beam-size method or a combination of them.

In the abovementioned optical reading apparatus, the laser beam is focused onto the subject, and the light diffused and reflected from the subject is collected and guided to the multi-segmented photo-diode. Then, the distance relationship between the subject and the multi-segmented photo-diode is determined based on the difference between the outputs of photo-segments included in the multi-segmented photo-diode. When the distribution of reflecting rates caused by the density contrast resides on the surface of the subject, the calculation result for the abovementioned difference information falls into disorder. However, since the sum of the output values of photo-segments included in the multi-segmented photo-diode is equivalent to the distribution of reflecting rates, it becomes possible to remove the noise components caused by the density contrast of the subject from the output of the multi-segmented photodiode by utilizing the sum of them.

(30) The optical reading apparatus cited in any one of items 22–25 or items 27–29, characterized in that, an aperture member, which optically shades the noise components caused by optical factors, is disposed.

In the abovementioned optical reading apparatus, the aperture member is disposed at anywhere in the light path, in order to prevent the noise components caused by optical factors from entering into the photo-receiving element, or in order to reduce the amount of the noise components entering into the photo-receiving element. Further, specifically, when the photo-receiving area on the photo-receiving element is reduced by optimally disposing the aperture member, it is possible to reduce the low frequency noise components outputted in the time passage domain and which belong to the noise components caused by the optical factors. As mentioned above, by adjusting the light entering into the photo-receiving element, it becomes possible to remove the noise components having frequencies lower than a predetermined frequency.

(31) The optical reading apparatus cited in any one of items 22–25, characterized in that, a plurality of light sources are symmetrically disposed to reduce the influence of the noise components caused by the optical factors.

In the above optical reading apparatus, a plurality of light sources are symmetrically disposed to cancel the noise components caused by the optical factors with each of the light, and as a result, the influence of the noise components is suppressed.

(32) The optical reading apparatus cited in any one of items 22–25, characterized in that, a plurality of photo-receiving elements are symmetrically disposed, and the influence of the noise components caused by the optical factors is reduced by synthesizing or selecting the photo-receiving results of the plurality of photo-receiving elements.

In the above optical reading apparatus, a plurality of photo-receiving elements are symmetrically disposed, and the photo-receiving results of the plurality of photo-receiving elements are synthesized or selected to cancel the noise components caused by the optical factors, and as a result, the influence of the noise components is suppressed.

BRIEF DESCRIPTION OF THE DRAWINGS

Other objects and advantages of the present invention will become apparent upon reading the following detailed description and upon reference to the drawings in which:

FIG. 12(a) shows a perspective view of the aperture member, while FIG. 12(b) and FIG. 12(c) show cross-sectional views of the aperture member;

FIG. 13(a) and FIG. 13(b) show cross-sectional views, while FIG. 13(c) shows a graph of the detecting result;

DETAILED DESCRIPTION OF THE PREFERRED EMBODIMENT

Figure 1:
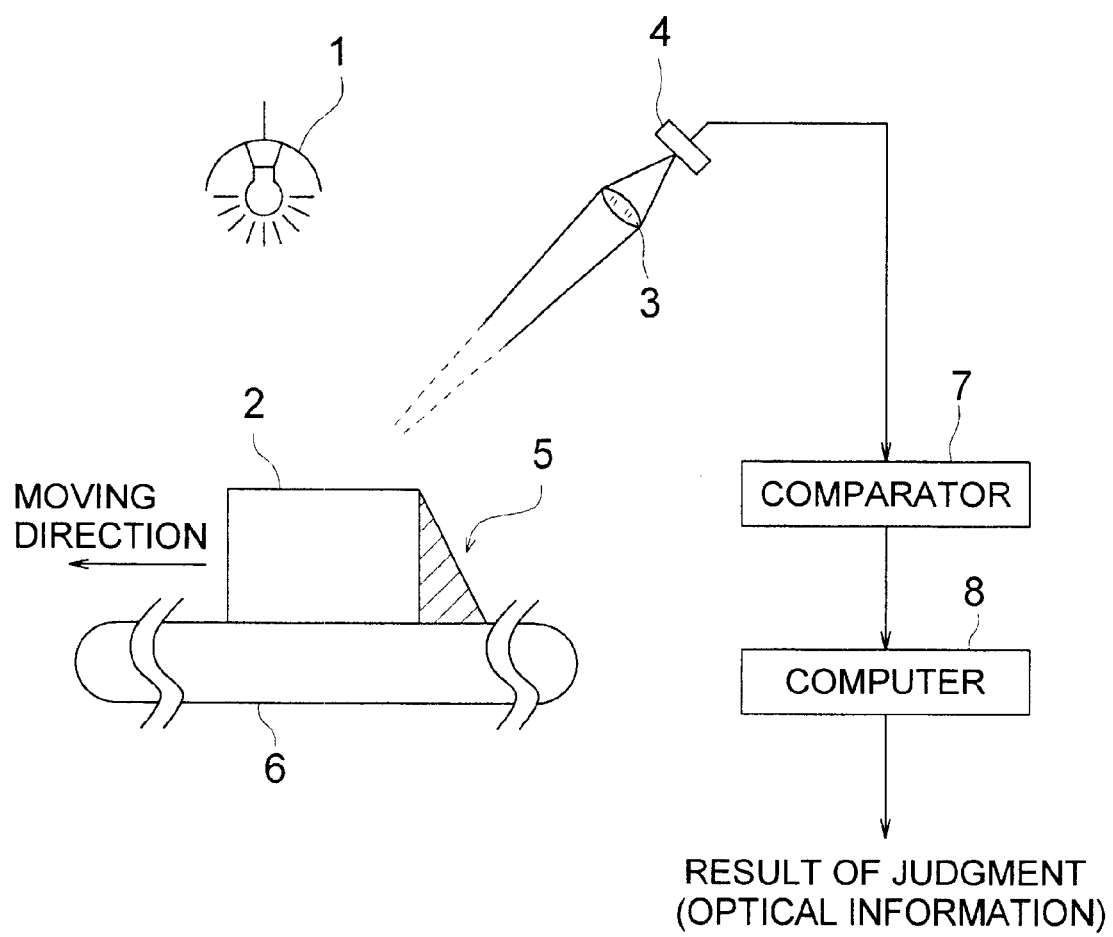
FIG. 1 shows a block diagram of an exemplified configuration of an optical reading apparatus embodied in the present invention.

Referring to the drawings, an embodiment of the present invention will be detailed in the following.

[First Embodiment]

FIG. 1 shows a block diagram of an exemplified configuration of an optical reading apparatus embodied in the present invention.

For instance, in a factory in which boxes made of paper materials (corrugated cardboard boxes, etc.) are handled, sometimes, the reflected light strength of the subject is measured, in order to perform an arithmetic processing for discriminating and classifying papers based on the reflecting rate of the paper.

The measurement is performed under light source 1, such as a room light, a fluorescent light in the vicinity, or illumination light equipped with the photo-receiving element, etc. In the configuration shown in FIG. 1, collecting lens 3 collects the light reflected from subject 2, and computer 8 stores the data, which are analogue-to-digital converted from the output signals of PSD 4 (Positioning Sensitive Detector 4), serving as a photo-receiving element. When shadow portion 5 of subject 2, such as a box, etc., arrives at the detecting position, the intensity of the received light abruptly decreases at shadow portion 5, and sometimes, computer 8 erroneously determines that subject 2, such as a box, etc., has a very low reflecting rate. To avoid the above drawback, comparator 7 eliminates data lower than a predetermined light intensity from the stored data by performing logical judgments. Then, computer 8 performs the arithmetic processing in regard to optical data from which the data equivalent to the shadow portion is eliminated. Thus, it becomes possible to precisely determine subject 2. Other than PSD 4, a CCD (Charge Coupled Device) and a PD (Photo Detector) can be employed for photo-receiving element.

Incidentally, it is desirable that the threshold value employed for comparator 7 is prescribed at an intermediate value between a minimum lightness value of the background color (overall reflecting rate) of the paint, etc., equipped on the surface of subject 2, and the lightness value of shadow portion 5.

Accordingly, in the first embodiment, the optical reading apparatus comprises at least a photo-receiving element, such as PSD 4, etc., and opt-electronically converts the received light in such a manner that the light reflected from subject 2 enters into PSD 4 under light source 1, such as the room light, etc., and applies processing, equivalent to mathematic logical calculations, such as a differential calculus, an integral calculus, sum and subtract calculus, etc., to noise components caused by an optical mechanism (in this embodiment, generated at the shadow portion) with simpler arithmetic elements and circuits, to obtain the optimum signals. In the first embodiment shown in FIG. 1, since, when data lower than a predetermined light intensity at the shadow portion is detected, the data is eliminated from the consecutive data by using the simple comparator, the optical reading apparatus can precisely recognize subject 2.

Incidentally, the abovementioned noise components caused by an optical mechanism can be classified in the following categories.

Noise Components Generated in the Optical System (1) When a coherent light is employed, light generated at an edge of an optical element due to the Fresnel diffracting action overlaps with the optical information as the noise components caused by the optical factors. In this case, provided that the distance from the edge of the optical element, at which Fresnel diffracting action occurs, to the photo-receiving element, the shape of the optical element, etc. are known, it is possible to reduce the noise components with a calculating result based on an equation of diffraction.

(2) In case of light reflected from the surface of the optical element (the surface of the lens) or reflected from the edge of the optical element (including the edge of the lens), it is possible to reduce the noise components included in the optical information by performing a practical measurement of its reflecting rate and a strict simulation in advance, and then, by calculating the noise components caused by the optical factors.

Noise Components Generated Outside the Optical System (3) In case of a shadow or a background light of the subject, distribution characteristics of luminous intensity of the background light is memorized in advance to subtract them from the optical information. For simplicity, it is also applicable not only to subtract predetermined values from the detected results, but also to cut and neglect the output value when the output value is less than that in the range of the original intensity.

The noise components caused by the optical factors, cited in any one of abovementioned items 1–3, can be eliminated by the arithmetic processing performed in computer 8, or can be electronically eliminated by the arithmetic operations performed by the operational amplifier, etc. equipped in an exclusive processing circuit.

Figure 2:
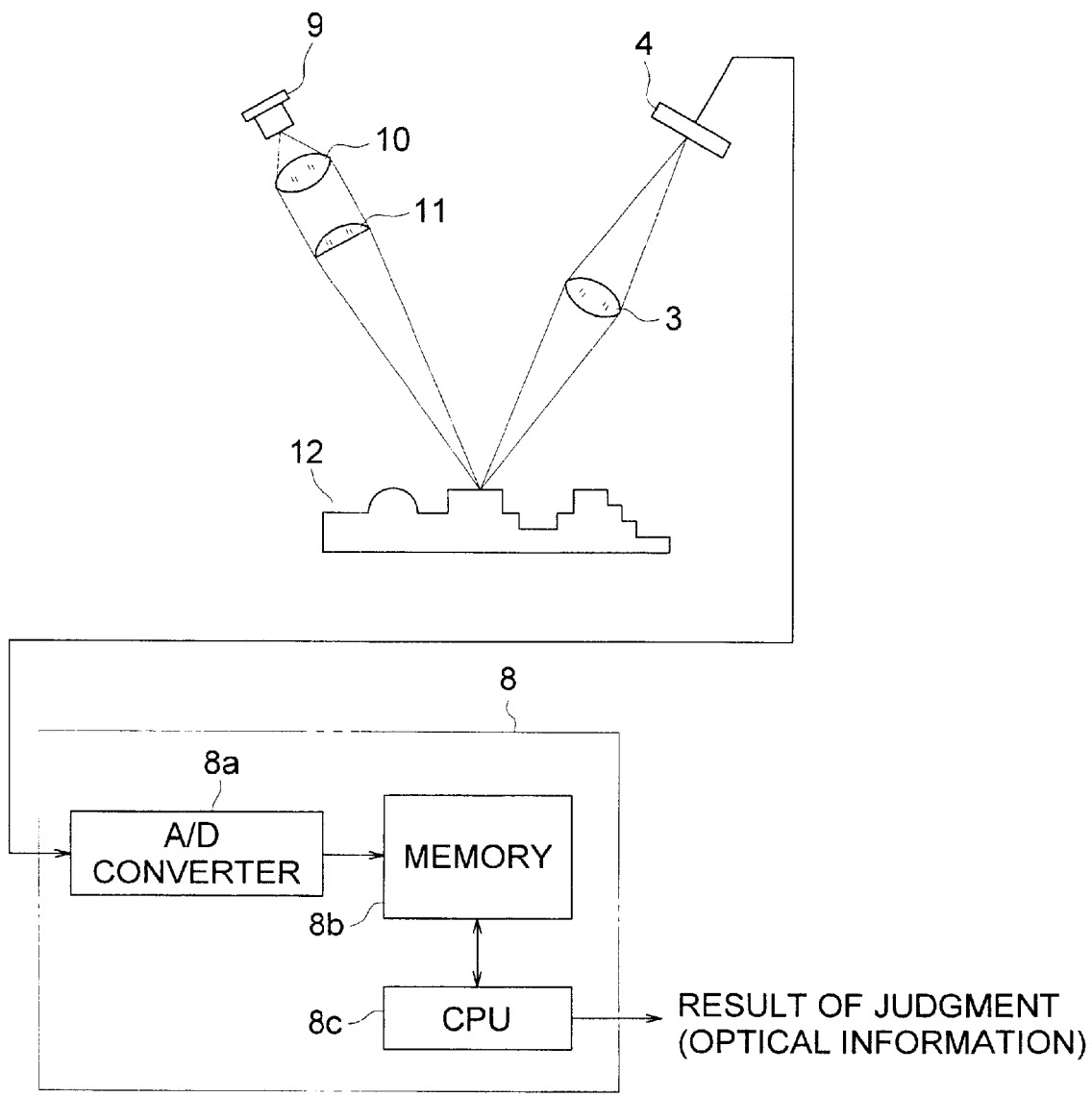
FIG. 2 shows a block diagram of an exemplified configuration of an optical reading apparatus embodied in the present invention.

When computer 8 determines and classifies subject 2 by measuring the light intensity reflected from subject 2 for the reflecting rate of subject 2, as shown in FIG. 2, it is desirable that A/D converter 8a converts the output analogue signals of PSD 4 to digital data, and memory 8b stores the digital data of the optical information, and CPU 8c performs the arithmetic processing based on software (execution of program) by using the stored digital data. In the above configuration, since a large amount of information are stored in a uniform format, it is possible to analyze the stored digital data with various kinds of methods, and to derive various kinds of information from them. Specifically, it sometimes becomes possible to eliminate noise components, etc., which cannot be separated from main signals by mechanical methods, by performing complicated arithmetic processing.

Incidentally, in the configuration shown FIG. 2, CPU 8c includes both functions of an elimination calculating means for reducing or eliminating the noise components, and a calculating means for performing arithmetic processing to detect the information of the subject under detection.

In the above simplified example, when the shadow portion arrives at the detecting position, the intensity of the received light abruptly decreases, and therefore, the computer erroneously determines that the subject has a very low reflecting rate. To avoid the above drawback, the data lower than a predetermined light intensity is reduced from the stored data at the initial stage of the arithmetic processing by performing logical judgments. In this method, the signals are initially processed to obtain waveforms without noise components, namely, the noise components are initially removed from the original signals by calculating with data stored in the memory. Accordingly, since the signals, from which noise components are already removed, are encoded into binary or multivalued data to conduct the image processing, it is possible to precisely detect the information under the detecting operation, and further, the abovementioned method is superior to conventional methods for discriminating a shape or letters by applying an arithmetic filtering processing afterward to two-dimensional information stored in advance.

Figure 3:
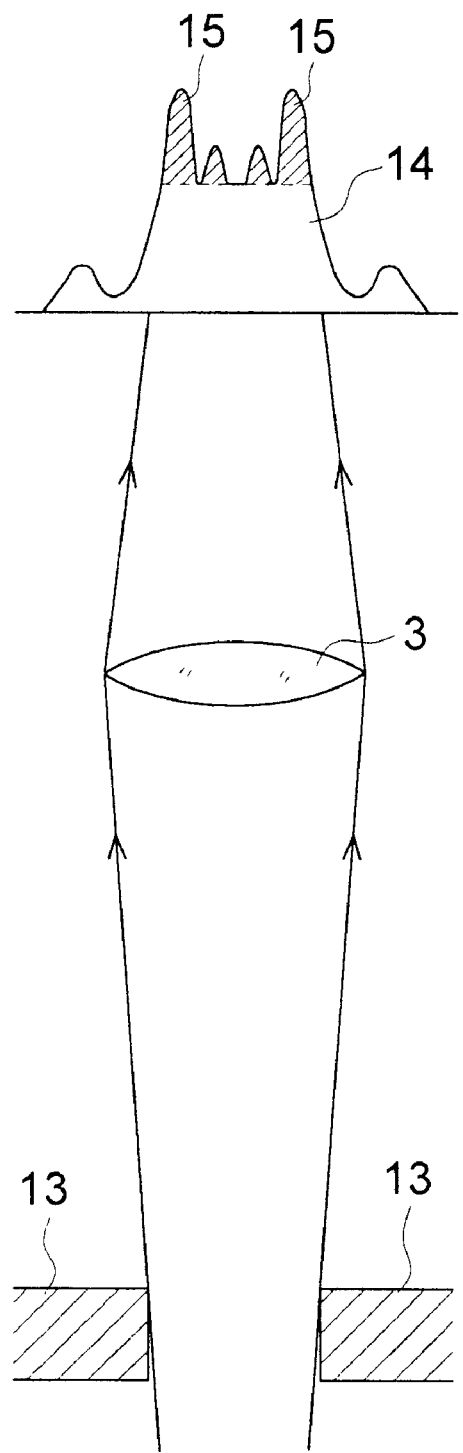
FIG. 3 shows an explanatory illustration of a light diffracting action generated at edges of an optical system of an optical reading apparatus embodied in the present invention.

Further, as a concrete example of the configuration shown in FIG. 2, there will be exemplified the apparatus, in which the photo-receiving element is a PSD or the like being detectable of the position of the received light, and the light source is a Laser Diode (a LD), and the irradiation light is a linear light obtained by shaping the light bundle, emitted from the light source, with cylindrical lens 11, etc., and the subject is card 12, which moves at a constant velocity and comprises at least one of a concave and a convex, and the received light, being the linear light corresponding to at least one of the concave and the convex, enters into PSD 4. Even in the above situation, since the light emitted from the light source is a laser beam, Fresnel diffraction component 15, generated by the edge, etc. of optical member (chasing) 13, overrides signal component 14, to be obtained as original signals, at the edge of PSD 4, as shown in FIG. 3.

Since CPU 8c calculates Fresnel diffraction component 15 in accordance with a theory for deriving the light diffraction from the distance between the edge at which the light is eclipsed and the photo-receiving element, and then, subtract the derived value from the output data of the photo-receiving element stored in memory 8b to obtain signal component 14, it becomes possible to perform precise measurements and judgments.

Figure 4:
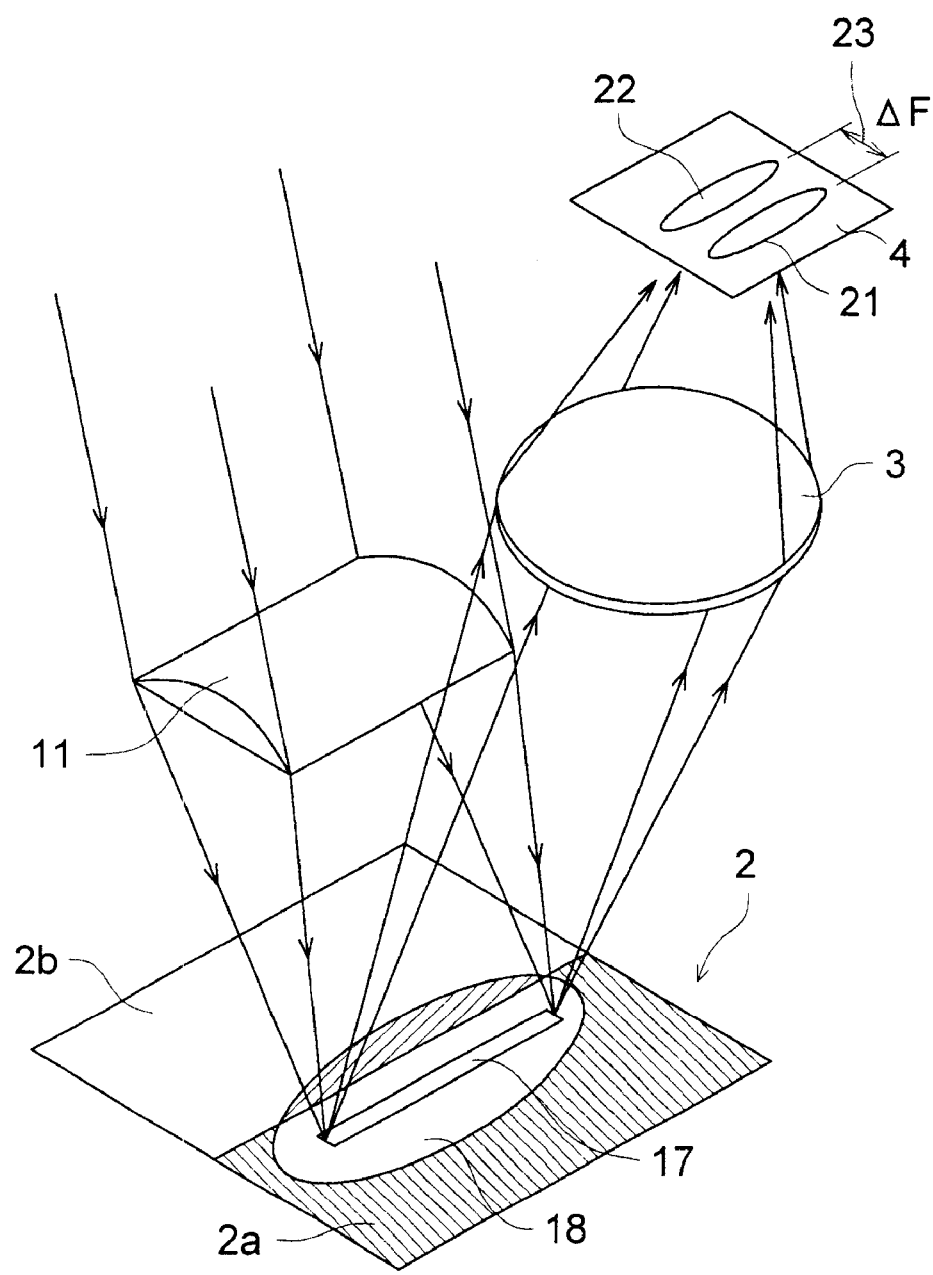
FIG. 4 shows a perspective view of an exemplified configuration of an optical reading apparatus embodied in the present invention.

Further, FIG. 4 shows a perspective view of the configuration of the apparatus embodied in the present invention. The irradiation light emitted from the light source is shaped into a liner light by cylindrical lens 11, and the liner light is irradiated onto subject 2. In FIG. 4, subject 2 is a card comprising black area 2a and white area 2b. In addition, the liner light comprises liner light center area 17, which is located at its center portion and has a strong light intensity, and liner light diffusion area 18, which is an area diffused around liner light center area 17 and has a relatively weak light intensity.

Still further, in the situation shown in FIG. 4, liner light center area 17 resides within black area 2a, while a part of liner light diffusion area 18 resides within white area 2b. In this case, a part of liner light diffusion area 18 enters onto white area 2b, and the light reflected from white area 2b is collected by collecting lens 3, so as to enter into PSD 4.

In FIG. 4, the light, entering into the incident surface of PSD 4, is illustratively indicated. Numeral 21 is a white image of white area 2b projected by liner light diffusion area 18, and numeral 22 is a black image of black area 2a projected by liner light center area 17.

Figure 5:
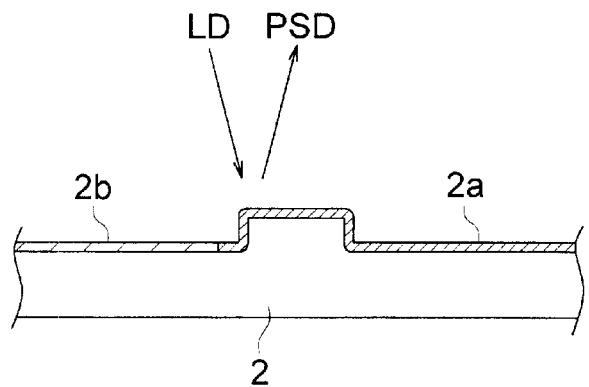
FIGS. 5(a)–5(c) show explanatory illustrations of noise components caused by optical factors.
Figure 5:
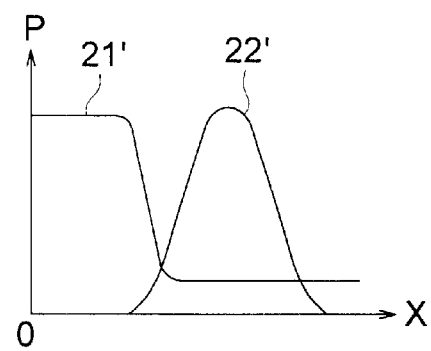
Figure 5:
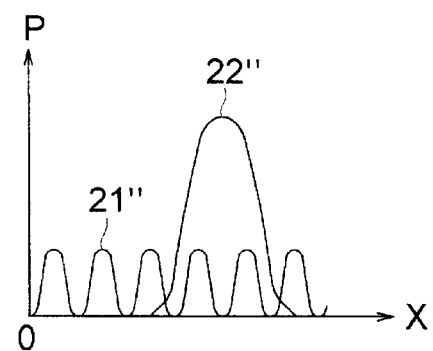

Incidentally, when the information of subject 2 under the detecting operation is information in respect to at least one of the concave and the convex on the surface, the light of liner light diffusion area 18 reflected from white area 2b generates the noise components caused by the optical factors. As mentioned above, in case that the noise components caused by the optical factors are the information other than the information of subject 2 under the detecting operation, and the information arise from the distribution of reflecting rates or the distribution of transmitting rates (refer to FIG. 5(a)), it is difficult to discriminate between the optical information detected from at least one of the concave and the convex on the surface of subject 2 and the optical information detected from the density variation on the surface of the subject (a pattern having color contrast, a pattern having different colors, such as black and white, etc., etc.). Further, the noise components emerge in response to the width pitch of the pattern and sometimes indicate movements, which would be resolved into the frequency domain, such as strengthening or weakening, etc. Accordingly, as shown in FIG. 5(b), the influence of noise components 21' caused by the optical mechanism can be reduced by performing the eliminating calculation processing before performing the arithmetic processing in the abovementioned configuration. Thus, it becomes possible to detect optical information 22', being necessary as a detecting object, without influenced by noise components 21'.

Incidentally, in the configuration shown in FIG. 4, CPU 8c, serving as an elimination calculating means, can detect the noise components based on the difference of frequency components of the digital data opt-electronically converted by PSD 4.

In other words, it becomes possible to reduce the influence of the noise components caused by the optical factors, and to improve the accuracy of the information, being necessary as a detecting object, by giving attention to the difference of frequency components and by detecting the noise components with using spatial low-pass and/or high-pass filters, etc., when performing the eliminating calculation processing before performing the arithmetic processing.

Figure 6:
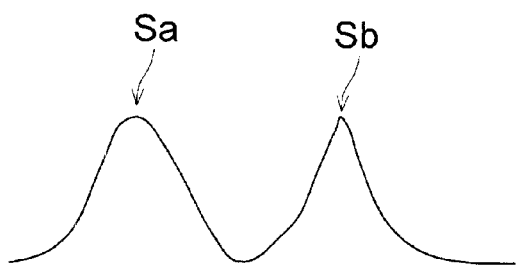
FIG. 6 shows an explanatory illustration of noise components caused by optical factors.

Incidentally, the effect of the abovementioned filters is different from that of electronic low-pass and/or high-pass filters. As shown in FIG. 6, signal Sa and signal Sb, both of which have approximately the same optical frequency, exist in appearance. Now, it is assumed that signal Sa represents the required signals derived from the convex or the concave of the card, while signal Sb represents the noise components caused by the optical factors. In this case, although signal Sa is caused by the optical variations having a frequency lower than that of signal Sb, sometimes, signal Sa and signal Sb emerge at the same frequency as a result. Therefore, the noise components cannot be eliminated by means of electronic filters, but can be eliminated only by calculating the optical data as mentioned above.

FIG. 5(c) exemplifies a case that the noise components caused by the optical factors are high frequency components. In this case, it is possible to detect optical information 22', being necessary as a detecting object, by utilizing the deference between frequency components and by reducing the influence of noise components 21' caused by the optical mechanism.

[The Second Embodiment]

The second embodiment, in which an operation for separating the optical information, being as a detecting object, from the noise components caused by the optical factors is performed based on the centroid of the reflected light, will be detailed in the following.

Even in the second embodiment, there is employed the optical reading apparatus, characterized in that the influence of the noise components is reduced by calculating quasi surface deviations of the convex or the concave (hereinafter, referred to as the quasi-deviation) including noise components associating with the distribution of reflecting rates caused by the density variation, which are the same kind of non-detected information of the subject, aforementioned referring to FIG. 2 and FIG. 4.

Generally speaking, in the operation for optically reading the information with the reflected light, the variation of reflecting rates on the surface of the subject caused by the information, being different from the information of the detecting object, could be the cause of a big confusion in respect to the information of the detecting object. Specifically, when other signals (quasi-signals), the amplitude of which is equivalent to or larger than that of the original signals to be obtained, is outputted from the photo-receiving element in a state of overlapping each other, it is virtually impossible to eliminate the quasi-signals in advance only by its mechanism and/or optical configuration. It becomes possible, however, to reduce the noise components, disturbing as the quasi-signals, by performing the steps of storing the signals outputted from the photo-receiving element into memory 8b, deriving the information in regard to the variation of reflecting rates on the surface of the subject (the information by the quasi-deviations) in the arithmetic processing operation of CPU 8c, and removing the information from the signals outputted from the photo-receiving element. Incidentally, in this case, the arithmetic processing operation performed by CPU 8c is a kind of the simulation calculating operation.

An apparatus, in which the photo-receiving element is such the element as PSD 4 being capable of detecting the centroid of the received light, the light source is the LD (Laser Diode), the illumination light is a linear light formed by shaping the light bundle emitted from the light source with the cylindrical lens, etc., the subject 2 is a card-type subject, which moves at a constant velocity and comprises at least one of a concave and a convex, and PSD 4 can receive the linear light corresponding to the convex or the concave projected on PSD 4, is assumed as a concrete example of the second embodiment. Incidentally, when a one-dimensional PSD is employed for the PSD serving as a photo-receiving element, two electronic currents can be obtained from the both ends of the photo-receiving element. In this case, it is possible to derive the centroid position of the light received on the PSD from the arithmetic processing of the value, obtained through the processes of the I/V conversion, the amplifying operation and the A/D conversion of the two electronic currents. Further, by image-processing the information of the centroid position by means of calculating means such as CPU 8, etc., and recognizing the information as the convex or the concave, it is possible to distinguish the information of characters, numerals, etc. formed in either the convex or the concave by embossing the subject.

Figure 15:
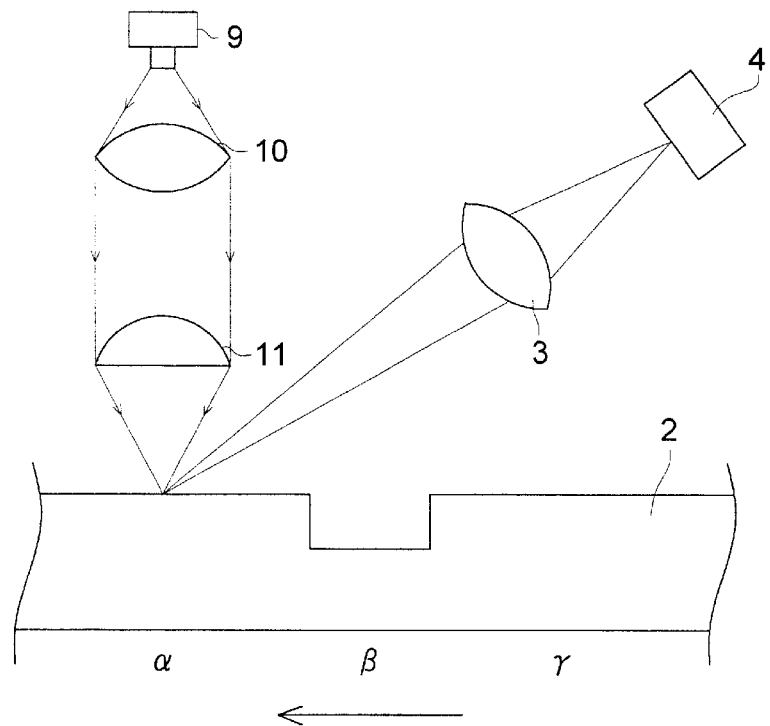
FIG. 15 shows an embodiment of an optical reading apparatus for detecting the distribution of the concave variations of the card comprising plain portion α and concave portion β.
Figure 16:
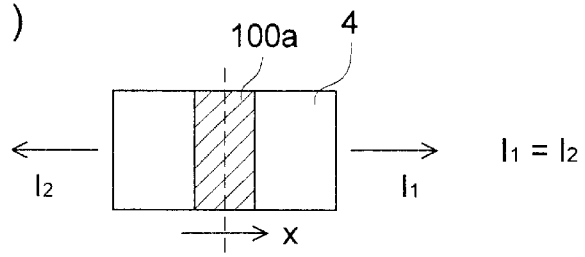
FIGS. 16(a)–16(c) show variations of the light spot projected on the PSD (Positioning Sensitive Detector)
Figure 16:
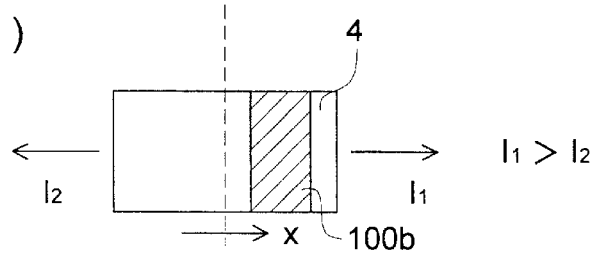
Figure 16:
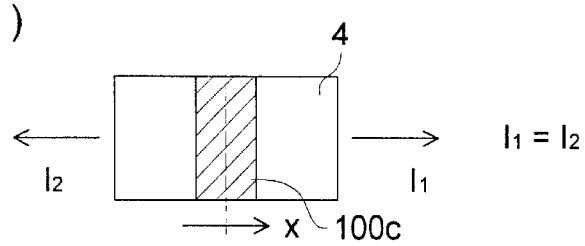

For instance, FIG. 15 shows an embodiment of an optical reading apparatus for detecting the distribution of the concave variations of card 2 comprising plain portion α and concave portion β. In FIG. 15, the positions of PSD 4, collecting lens 3, etc. are determined at such positions that the light, reflected from plain portion α, forms spot 100a at substantially the center of PSD 4, as shown in FIG. 16(a), when the light emitted from LD 9 is irradiated onto plain portion α. In the above case, the two electronic currents outputted from the both ends of the PSD 4 exhibit the same value due to the property of the PSD (in FIG. 16(a), $I_1=I_2$). In other words, the centroid position of the reflected light is located at the center of PSD 4. Further, when subject 2 moves in the direction designated by the arrow and the light emitted from LD 9 is irradiated onto concave portion β, the light reflected from concave portion β forms spot 100b at a position shifted from the center of PSD 4, as shown in FIG. 16(b). Then, the two electronic currents outputted from the both ends of PSD 4 exhibit different values, namely, the value of the electronic current outputted from the end near the spot 101b is greater than that outputted from the other end of PSD 4 (in FIG. 16(b), $I_1>I_2$). In other words, the centroid position of the reflected light is located at the position shifted from the center of PSD 4. Still further, when subject 2 moves in the direction designated by the arrow and the light emitted from LD 9 is irradiated again onto plain portion γ, the light reflected from plain portion γ forms spot 100c at substantially the center of PSD 4 as well as the case of irradiating the light onto plain portion α, as shown in FIG. 16(c). In this case, the two electronic currents outputted from the both ends of PSD 4 also exhibit the same value (in FIG. 16(c), $I_1=I_2$). Accordingly, the distribution of displacement variations on the concave portion can be detected from the variations of the abovementioned values of the electronic current. As mentioned above, displacement information of the photo-receiving position can be obtained by employing the PSD, and thereby, the distribution of displacement variations on the concavo-convex portion can be detected. However, considering such a case that the light intensity at a light irradiating point varies depending on the reflecting rates or the transmitting rates of the subjects, it is desirable that the value derived from $(I_1-I_2)/(I_1+I_2)$, instead of the value derived from $(I_1-I_2)$, is employed as the displacement information of the subject. In other words, the equation of $X_A=(I_1-I_2)/(I_1+I_2)$ gives the displacement information of the subject at the light irradiating point. Further, $X_A$ can be regarded as a value, which indicates the centroid position of the light on PSD 4 in its X-direction.

CPU 8c calculates the centroid position of the reflected light of the noise components (noise components caused by the optical factors), disturbing as the quasi-signals, from the optical information being in proportion to the distribution of reflecting rates by performing the elimination calculating processing, and subtracts the calculated result from the centroid position of the reflected light, which is directly derived from the light received on the PSD at first by performing the calculating processing. Then, it is possible to obtain the high-accurate optical information of at least one of the convex and the concave by performing a normal arithmetic processing in respect to the signals in which the noise components caused by the optical factors are reduced.

Incidentally, PSD 4 has a plurality of output ports to calculate the centroid position of the received light. In reality, the one-dimensional PSD outputs two electronic currents from its both ends, each of which is in inverse proportion to the distance from the end to the centroid position of the light received on the element. Further, the sum of the two electronic currents is in proportion to the intensity of the light reflected from the surface of the card after emitted from the LD, serving as a light source, and the information of the sum of the outputs in a time passage domain can be regarded as being equivalent to the information of the distribution of reflecting rates. The approximate noise components, serving as quasi-signals of outputs of PSD 4, can be obtained by applying a predetermined arithmetic processing to the information mentioned above.

The above processing will be detailed in the following.

Figure 17:
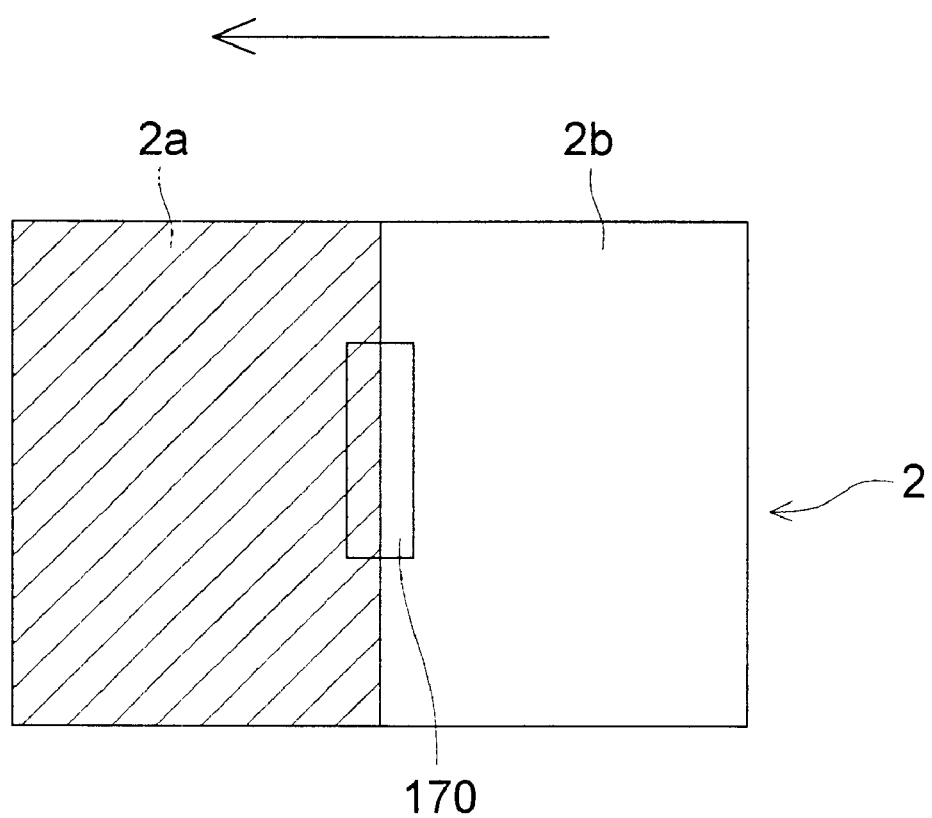
FIG. 17 shows a surface of the card, which comprises a bright portion and a dark portion.
Figure 18:
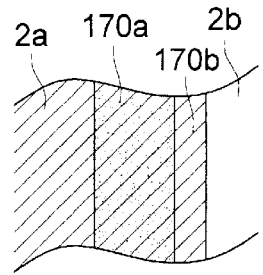
FIGS. 18(a)–18(e) show variations of a linear light spot, varying with time, on the surface of the card.
Figure 18:
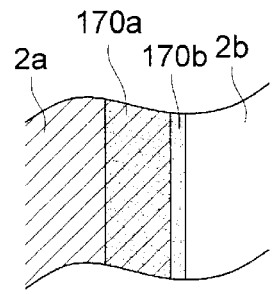
Figure 18:
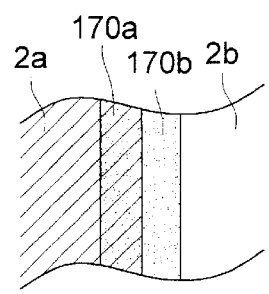
Figure 18:
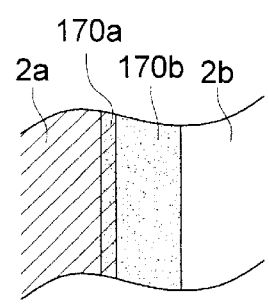
Figure 18:
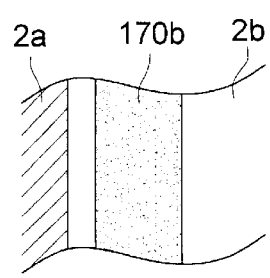
Figure 19:
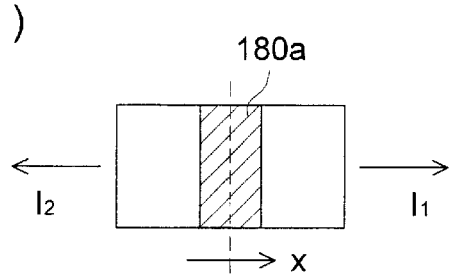
FIGS. 19(a)–19(e) show variations of the light spot received on the PSD with time.
Figure 19:
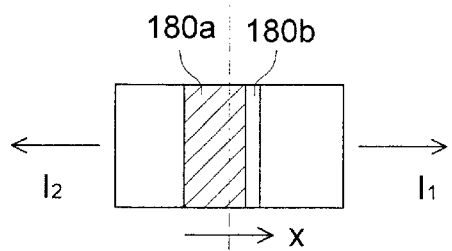
Figure 19:
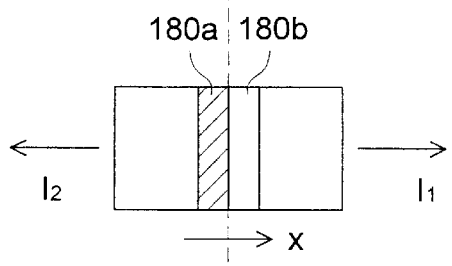
Figure 19:
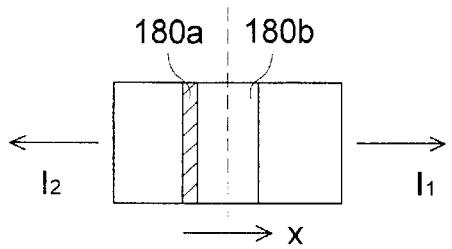
Figure 19:
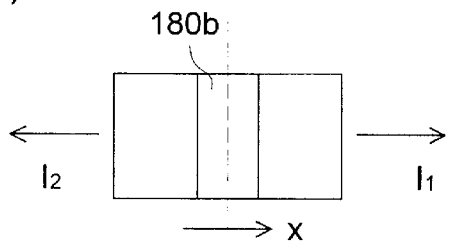

As shown in FIG. 17, it is assumed that the surface of card 2 comprises a bright portion (white area 2b), from which more than 90% of the incident light is reflected or diffused, and a dark portion (black area 2a), from which less than several % of the incident light is reflected or diffused, and linear light spot 170 is irradiated onto the surface of card 2 by using the apparatus shown in FIG. 15. Further, card 2 moves in a direction designated by the arrow.

FIGS. 18(a)–18(e) show variations of linear light spot 170 varying with time, when linear light spot 170 moves in the vicinity of the border of white area 2b and black area 2a, both of which are a plain surface, under the abovementioned situation. At that time, linear light spot 170 is reflected by the surface of card 2, and the reflected light is received on PSD 4 (in this embodiment, the one-dimensional PSD). FIGS. 19(a)–19(e) show variations of the light spot received on PSD 4 with time.

As shown in FIG. 18(a), all of linear light spot 170 initially resides within black area 2a. Since black area 2a is a plain portion, the light spot should be formed at substantially the center of PSD 4, as described referring to FIG. 16(a). As shown in FIG. 19(a), light spot 180a being slightly dark is formed at substantially the center of PSD 4, where $I_1=I_2$. In other words, in this state, the centroid of the received light resides just at the center of PSD 4.

As shown in FIG. 18(b), when card 2 moves in a direction designated by the arrow, a part of linear light spot 170b irradiates white area 2b, though almost of all linear light spot 170a still irradiates black area 2a. Even in this situation, since linear light spot 170, including linear light spots 170a, 170b, irradiates the plain portion, the light spot should be formed at substantially the center of PSD 4, as described referring to FIG. 16(a). As shown in 19(b), although the light spot is surely formed at substantially the center of PSD 4, the light spot comprises a small area being bright section 180b and a large area being a slightly dark section 180a. Since PSD 4 can detects not only a position of receiving the light, but also a quantity of the light, the relationship between electronic currents $I_1$ and $I_2$ outputted from PSD 4 can be established as $I_1>I_2$, due to unevenness of the brightness intensity within the light spot. Accordingly, PSD 4 detects the position of the light spot as if it would deviate from the center to the right direction (+x direction from the center), resulting in generation of noise components due to the distribution of reflecting rates caused by the density contrast of card 2. In addition, it can be stated for this situation that the centroid of the light deviates from the center to the right direction (+x direction from the center) (in the drawing).

As shown in FIG. 18(c), when card 2 further moves in a direction designated by the arrow, although a half of linear light spot 170a still irradiates black area 2a, the other half of linear light spot 170b irradiates white area 2b. Even in this situation, since linear light spot 170, including linear light spots 170a, 170b, irradiates the plain portion, the light spot is formed at the center of PSD 4, as shown in FIG. 19(c). However, the light spot comprises bright section 180b and dark section 180a, which are divided by the border located at substantially the center of PSD 4. Since the relationship of $I_1>I_2$ can be established due to unevenness of the brightness intensity within the received light spot, PSD 4 detects the position of the light spot as if it would deviate from the center to the right direction. Incidentally, since the bright section shown in FIG. 19(c) is larger than that shown in FIG. 19(b), $X_A=(I_1-I_2)/(I_1+I_2)$ in FIG. 19(c) is smaller than that in FIG. 19(b), namely, the deviation of the centroid of the light in FIG. 19(c) is less than that in FIG. 19(b).

As shown in FIG. 18(d), when card 2 further moves in a direction designated by the arrow, although a small area of linear light spot 170a still irradiates black area 2a, a large area of linear light spot 170b irradiates white area 2b. Accordingly, the light spot, formed on PSD 4, comprises the large area of bright section 180b and the small area of dark section 180a. Since the relationship of $I_1>I_2$ can be established, PSD 4 detects the position of the light spot as if it would deviate from the center to the right direction. Incidentally, since the bright section shown in FIG. 19(d) is larger than that shown in FIG. 19(c), $X_A=(I_1-I_2)/(I_1+I_2)$ in FIG. 19(d) becomes smaller than that in FIG. 19(c).

As shown in FIG. 18(e), when card 2 further moves in a direction designated by the arrow, all of linear light spot 170b irradiates white area 2b. Accordingly, the light spot, formed on PSD 4, only includes bright section 180b. Since the light spot, having a uniform light intensity, is formed at the center of PSD 4, the relationship of $I_1=I_2$ can be established and PSD 4 detects that the light spot resides at the center of PSD 4. Namely, it can be stated that the centroid position of the light returns to the center of PSD 4.

As mentioned in the above, when card 2, serving as a subject under detecting, has a distribution of reflecting rates, such as the density contrast, etc., and when the irradiating light moves in the vicinity of the border of the density contrast, the centroid position of the light $X_A=(I_1-I_2)/(I_1+I_2)$ varies on PSD 4, even if the light is irradiated on the plain portion of card 2.

Figure 20:
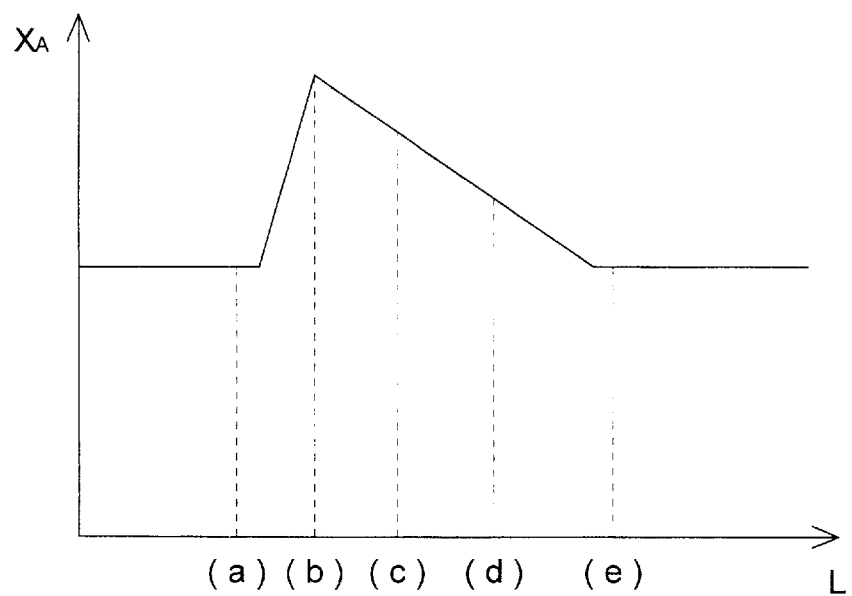
FIG. 20 shows a graph of the variation of the centroid position versus the moving position of the card, indicating moving distance L of the card in the horizontal axis and the centroid position of the light in the vertical axis, respectively.

FIG. 20 shows a graph of the variation of centroid position XC versus the moving position of card 2 in the example shown in FIGS. 18(a)–18(e) and FIGS. 19(a)–19(e), indicating moving distance L of card 2 in the horizontal axis and centroid position XC of the light in the vertical axis, respectively. In this example, since the light is always irradiated onto the plain portion, the waveform portion illustrated in FIG. 20 represents noise components generated by the distribution of reflecting rates caused by the density contrast of card 2, namely, the quasi-signals. Further, if the concavo-convex portion resides around the vicinity of the border of the white area and the black area, the quasi-signals overlap with the information generated from the concavo-convex portion serving as a detecting object. Incidentally, each position of symbols (a)–(e) indicated in FIG. 20 correspond to each of FIGS. 18(a)–18(e) and FIGS. 19(a)–19(e).

As mentioned above, at centroid of the light on the photo-receiving element $X_A$, the information representing the distribution of reflecting rates of the subject overlap with the information representing the distribution of the concavo-convex deviations of the subject. Then, it becomes possible to extract the information of the centroid of the light caused only by the distribution of the concavo-convex deviations of the subject, by subtracting the centroid of the light caused by the distribution of reflecting rates from the centroid of the light received on the photo-receiving element $X_A$. In short, it becomes important to obtain the centroid of the light caused by the distribution of reflecting rates.

As a result of the intensive study, the present inventors have discovered that the centroid of the light caused by the distribution of reflecting rates can be derived from the sum of two electronic current or voltage values outputted from the both ends of the PSD. In other words, the present inventors have discovered that the centroid of the light caused by the distribution of reflecting rates can be derived from the information of a total light quantity of the light spot. That will be detailed in the following.

Figure 21:
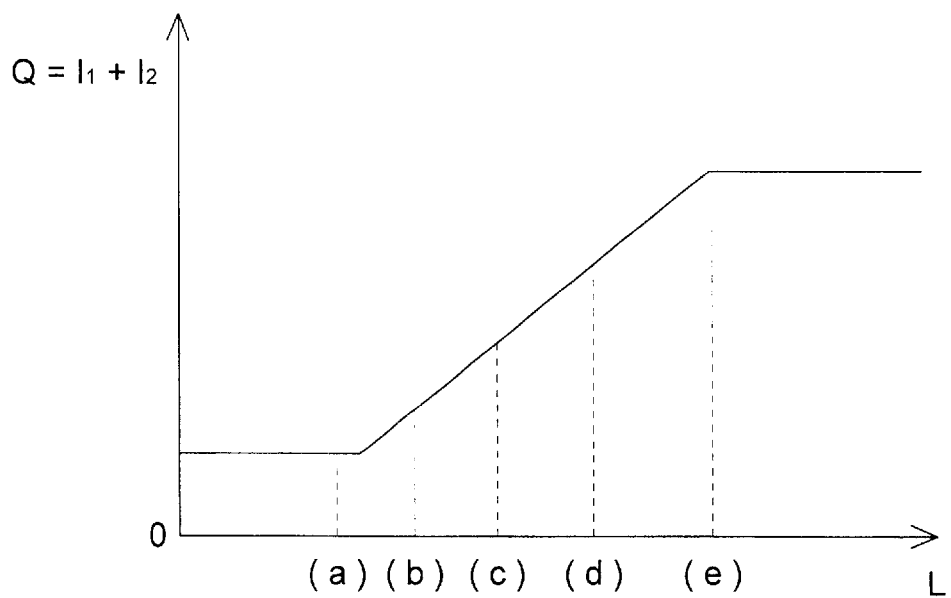
FIG. 21 shows a variation of the sum of two electronic current values versus the moving position of the card.

The quantity of the light irradiated onto the PSD is maintained at constant value, even if the light receiving position on the PSD varies in accordance with the concavo-convex deviations on the surface of the subject. On the other hand, the quantity of the light irradiated onto the PSD varies in accordance with the variations of the reflecting rate on the surface of the subject. Accordingly, the sum of two electronic current values (or voltage values), outputted from the both ends of the PSD, is irrespective of the concavo-convex deviations on the surface of the card, but varies in proportion to the reflecting rate on the surface of the subject. The example shown in FIGS. 17–20 is exemplified in the following explanation. FIG. 21 shows a variation (or a variation in a passage of time) of the sum of two electronic current values versus the moving position of the card in the example shown in FIGS. 17–20. The sum of two electronic current values can be also regarded as the total light quantity of the light spot on the PSD. In FIG. 20, moving distance L of the card is plotted on the horizontal axis, and sum Q $(=I_1+I_2)$ of two electronic current values is plotted on the vertical axis. Incidentally, each position of symbols (a)–(e) indicated in FIG. 21 correspond to each of FIGS. 19(a)–19(e)

Further, the sum of two electronic current values is corresponded to each moving distance L of the card, and for instance, sum Q at each moving distance L is memorized in a memory. The sums of two electronic current values are defined as $Q_1, Q_2, ---, Q_m, Q_{m+1}, Q_{m+2}, ---, Q_{m+u}, ---, Q_n$, each of which corresponds to each of the moving distances defined as $L_1, L_2, ---, L_m, L_{m+1}, L_{m+2}, ---, L_{m+u}, ---, L_n$. Incidentally, the width of the light spot on the card is "$L_{m+u}-L_m$".

Then, the centroid of the light caused by the distribution of reflecting rates can be derived from the above data. Since the variation of the centroid of the light caused by the distribution of reflecting rates occurs based on the unevenness of the light quantity within the light spot received on the PSD, it is possible to find the centroid of the light caused by the distribution of reflecting rates by determining the centroid of the light within the width of the light spot received on the PSD at each of the moving distances of $L_1, L_2, ---, L_m, L_{m+1}, L_{m+2}, ---, L_{m+u}, ---, L_n$. Further, provided that the width of the light spot is "$L_{m+u}-L_m$", when the moving distance is $L_m$, centroid XC(m) of the light within the width of the light spot received on the PSD, caused by distribution of reflecting rates, can be expressed as follow.

$$XC(m)=K\{((L_{m+1}-L_m)\cdot Q_{m+1}+ --- +(L_{m+u}-L_m)\cdot Q_{m+u})/(Q_m+Q_{m+1}+Q_{m+2}+ --- +Q_{m+u})$$

where K is a magnifying power of image formation.

Incidentally, as is clear in the above, it is desirable that the time interval for obtaining the sum of electronic current values is such an interval that the moving distance of the card during one interval is shorter than the width of the light spot.

Figure 22:
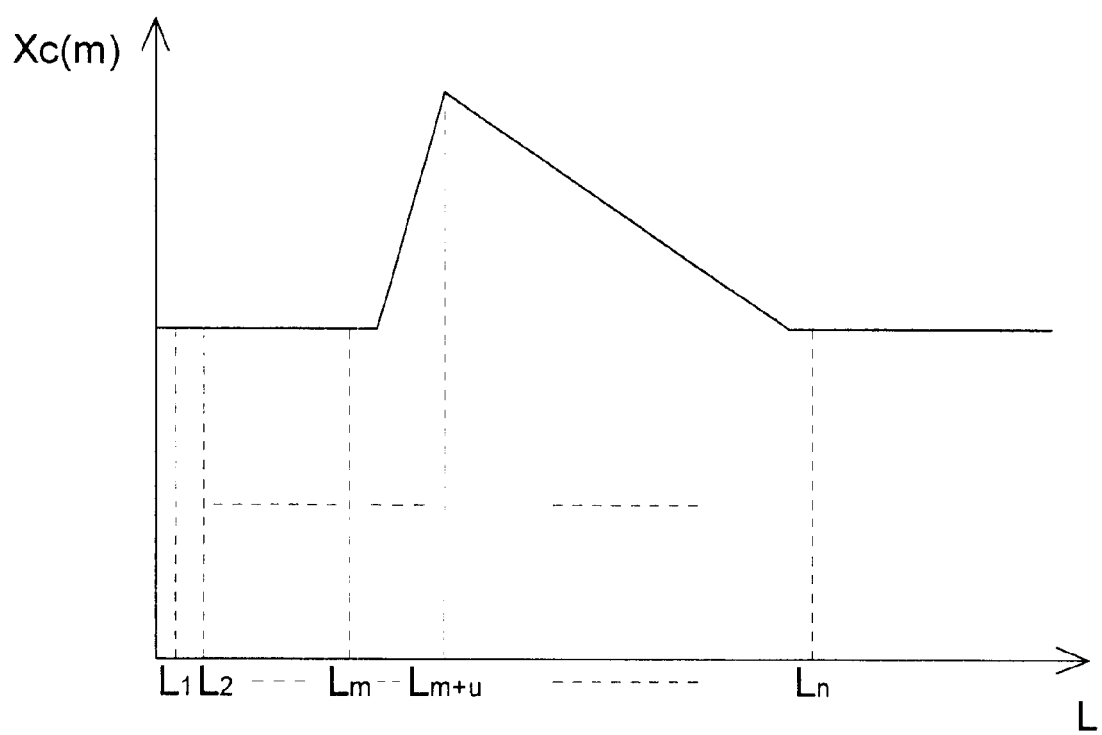
FIG. 22 shows a graph of the relationship between the moving distance and the centroid of the light within the width of the light spot received on the PSD.
Figure 23:
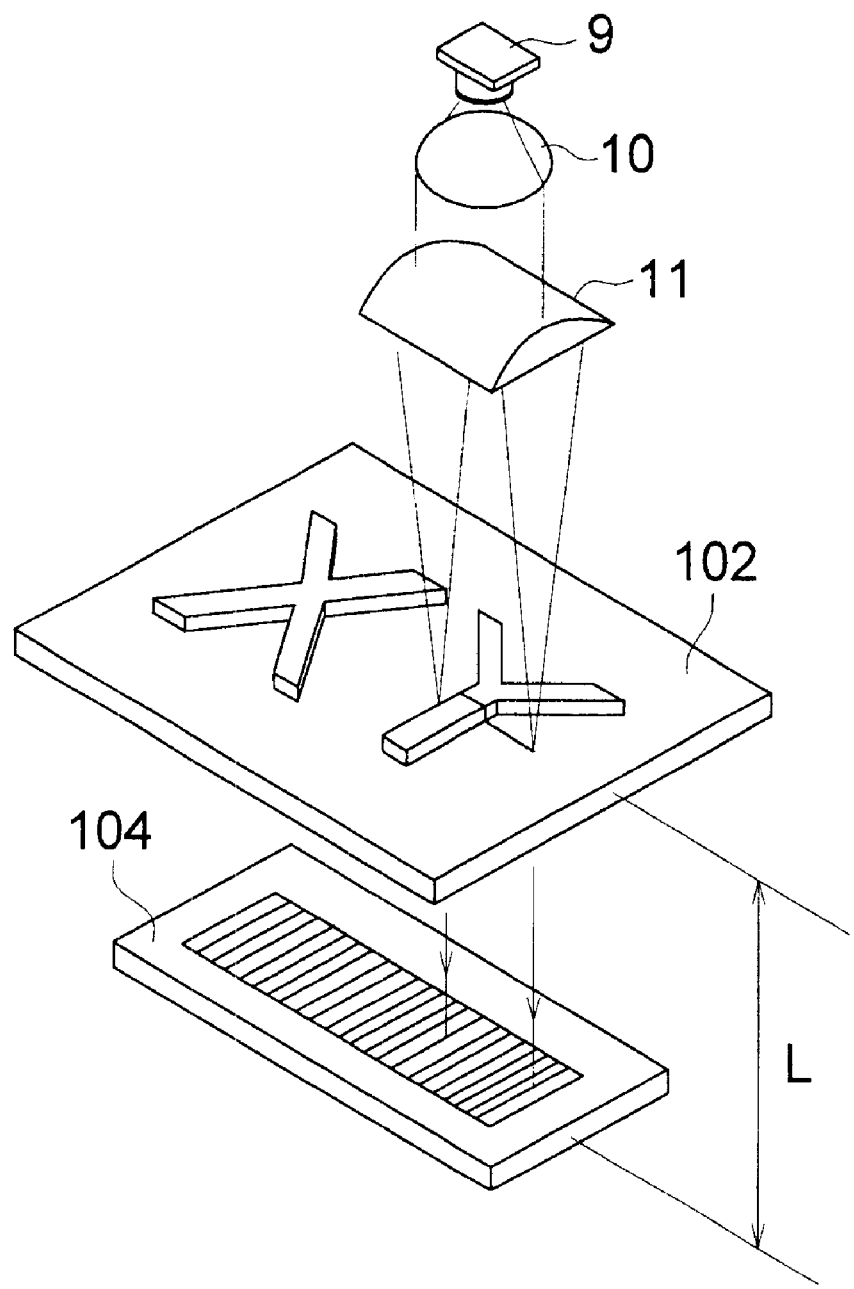
FIG. 23 shows an explanatory illustration for explaining an occurrence of the Fresnel diffraction generated by a transparent subject.

FIG. 22 shows a graph of the relationship between the moving distance and the centroid of the light within the width of the light spot received on the PSD (XC(m)), the centroid of the light being found at each of the moving distances of $L_1, L_2, ---, L_m, L_{m+1}, L_{m+2}, ---, L_{m+u}, ---, L_n$. Since the graph in respect to the plain portion having no concavo-convex is depicted in FIG. 20, the shape of the graph shown in FIG. 20 is substantially the same as that of the graph shown in FIG. 22. Accordingly, it becomes possible to find the information of the centroid of the light caused by the distribution of reflecting rates of the subject (XC(m)) from the sum of two electronic current values outputted from the both ends of the PSD. In other words, it is possible to find the information of the centroid of the light caused by the distribution of reflecting rates of the subject (XC(m)) from the information of the total light quantity of the light spot received on the PSD. Since the sum of two electronic current values outputted from the both ends of the PSD is a value irrelevant to the concavo-convex property of the subject as aforementioned, it is possible to obtain only the information of the centroid of the light caused by the distribution of reflecting rates of the subject (XC(m)), irrespective of the concavo-convex property of the subject. In other words, it is possible to obtain only the information of the noise components generated by the distribution of reflecting rates of the subject caused by the density contrast on the surface of the subject.

Further, as aforementioned, it is possible to find the information of the centroid of the light caused by the distribution of concavo-convex deviations of the subject by subtracting the information of the centroid of the light caused by the distribution of reflecting rates of the subject (XC(m)), which are derived from the sum of two electronic current values outputted from the both ends of the PSD, from the information of the centroid of the light received on the photo-receiving element ($X_A$), in which the information indicating the distribution of reflecting rates of the subject overlap with the information designating the distribution of concavo-convex deviations of the subject. In other words, it becomes possible to obtain the signals in which the noise components are reduced. The calculating processing means performs the abovementioned processing, and then, the calculating processing means conducts calculating processing for the signals, in which the noise components are reduced, to detect the information of the distribution of concavo-convex deviations of the subject.

Incidentally, the photo-receiving element is not limited to the one-dimensional PSD. For instance, such as a PD array, etc., can be employed. Further, it is desirable that the calculating processing means or the subtracting processing means comprises a MPU (micro processing unit), a CPU (central processing unit), a Customized LSI, a Gate Array, etc. Still further, it is desirable that the subtracting processing means also comprises a memory, for which an analogue memory and/or a digital memory can be employed. When employing a digital memory, it is desirable that the signals, generated by the opt-electronic converting action of the photo-receiving element, are converted to digital data by the analogue-to-digital converting operation to store the digital data in the digital memory. When employing a analogue memory, the signals, generated by the opt-electronic converting action of the photo-receiving element, can be directly stored in the analogue memory without performing the analogue-to-digital converting operation. Further, instead of the cylindrical lends shown in FIG. 15, a collecting lens having no directivity in the light collecting action can be also employed.

The abovementioned contents will be further detailed in the following, citing expressions being different form the above.

It is assumed that the card comprises a bright surface portion, from which more than 90% of the incident light can be reflected or diffused, and a dark surface portion, from which less than several percent of the incident light can be reflected or diffused. The intensity of the light is attenuated as the irradiated linear light leaves from its center. However, when an optical system without performing a sufficient aberration compensation is employed, the width of the low intensity area of the light unexpectedly becomes large.

When the widened light of linear light diffusion area 18 shown in FIG. 4 enters onto the high-reflective portion on the card (white area 2b) located at the side area of linear light center area 17, shown in FIG. 4 and serving as a main linear light, the intensity of the light reflected from white area 2b is more than or equal to that reflected from the low-reflective portion on the card (black area 2a), and collecting lens 3 collects the reflected light onto PSD 4. In this case, since PSD 4 receives the light including the abovementioned component, PSD 4 outputs such signals that the centroid of the light is located at a position, which is separated at distance ΔF (refer to FIG. 4) from the position, at which the image of linear light center area 17 is formed, in the side area on which the image of the high-reflective portion on the card (white area 2b) is formed (refer to FIG. 7).

Figure 7:
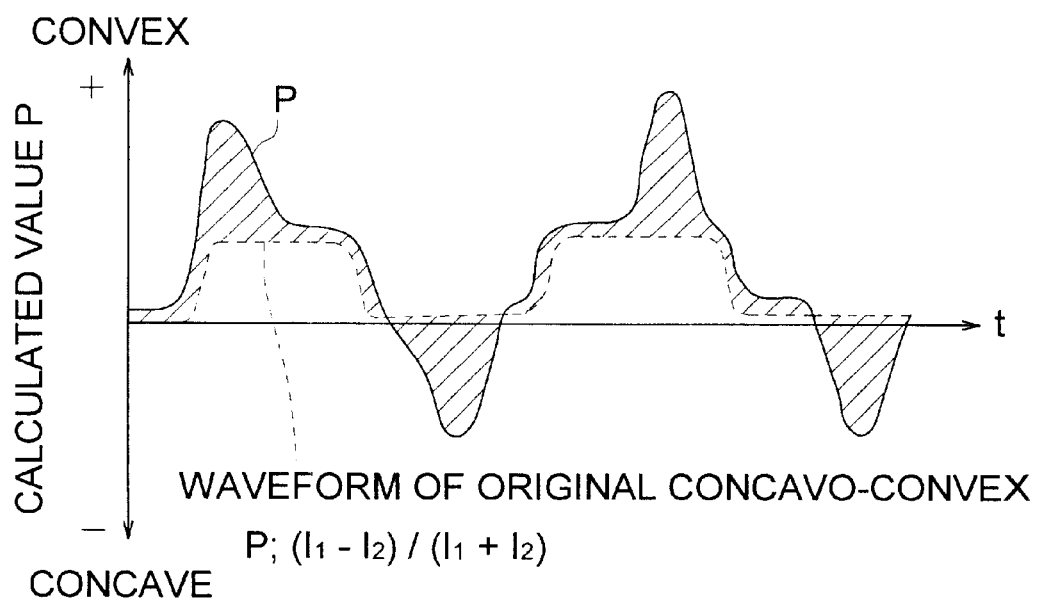
FIG. 7 shows an explanatory illustration of noise components caused by optical factors.

Incidentally, the solid line of FIG. 7 shows waveform P in a passage of time, which is derived from the equation of $$P=\{(I_1-I_2)/(I_1+I_2)\},$$

where $I_1$ and $I_2$ are two electronic current values outputted by PSD 4. Further, the broken line of FIG. 7 shows a waveform, which would be an ideal waveform to be obtained in respect to at least one of the essential convex or the essential concave.

The method for reducing the noise components, which generate the abovementioned ΔF, by means of an elimination calculating processing will be detailed in the following.

When employing the one-dimensional PSD, electronic current values, being in inverse-proportion to the intensity of the light and the distance to the centroid position of the light, can be derived from the both ends of PSD 4. The sum of the two electronic current values is simply the same as the output value of a single PD (Photo Detector). When the surface of the card is scanned by the linear light having an always constant intensity or a simply small spot light, the sum of the two electronic current values outputted from the both ends of PSD 4 is in proportion to the reflecting rate of the light, emitted from the LD serving as a light source, at the surface of the card. Further, although fine frequency components override on the distribution of real reflecting rates, the time passage distribution of the sum of the output values indicates a coarse approximation of the distribution of real reflecting rates. When the centroid of the light is found from the time passage distribution of the sum of the two output values, the centroid position of the quasi-signals caused by the distribution of reflecting rates is found as an independent value hardly relating to the centroid position by the essential linear light. This quasi-signals are main components of the noise, and it is possible to precisely obtain the original signals by simply removing this approximated quasi-signals.

When positions of receiving light on PSD 4 are defined as X1, X2, - - - , Xn, intensities of the light at each of the positions of X1, X2, - - - , Xn are defined as P1, P2, - - - , Pn, and the light of the noise components (noise components caused by the optical factors) is uniformly received on PSD 4, the centroid position XC of the light can be found from the following equation.

$$\Delta F = XC = (X1P1+X2P2+ \text{- - -} +XnPn)/(P1+P2+ \text{- - -} +Pn)$$

Figure 8:
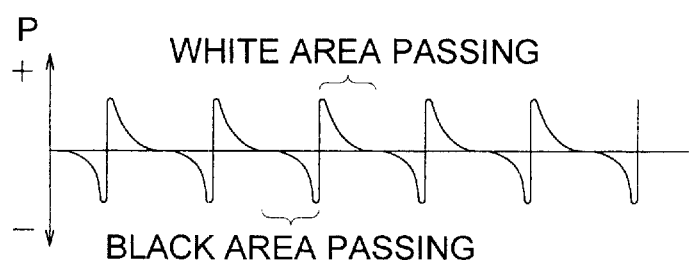
FIG. 8(a) and FIG. 8(b) show explanatory illustrations of noise components caused by optical factors.
Figure 8:
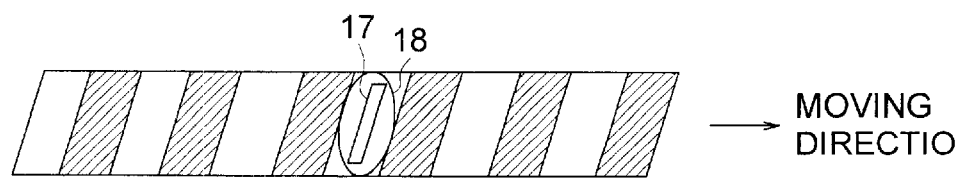

Incidentally, when subject 2 has a black and white stripe pattern as shown in FIG. 8(b), calculated value P depicts a carve like a triangle waveform as shown in FIG. 8(a).

Although the light of uniform noise components is received on the PSD in the above stage, this condition is only for a coarse approximation. More precise calculation can be performed by employing the distribution of luminous intensity of the illuminating light in the moving direction of the subject when conducting the calculation. When positions distributed on PSD 4 in a short side direction of the linear light (a moving direction of the subject) are defined as X1, X2, - - - , Xn, luminous intensities of the linear light projected on PSD 4 are defined as S1, S2, Sn, and the light of the noise components is uniformly received on PSD 4, the centroid position XC of the light can be found from the following equation.

$$\Delta F = XC = (X1P1S1+X2P2S2+ \text{- - -} +XnPnSn)/(P1S1+P2S2+ \text{- - -} +PnSn)$$

The abovementioned contents could be explained by citing the principle described as follow.

It can be considered that PSD 4 works as a kind of a low-pass filter in respect to the aforementioned distribution of reflecting rates, namely, components calculated from the light received on all area of the PSD 4. As aforementioned, however, PSD 4 works in reality based on complicated actions being different from those of electronic low-pass filters.

Figures 9D, 9E, 9F:
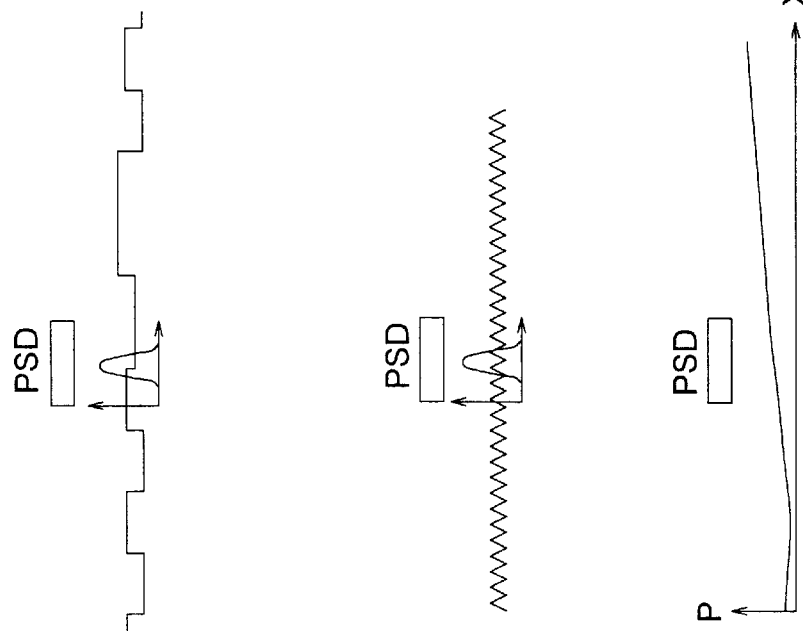
FIGS. 9(a)–9(f) show explanatory illustrations for explaining operations of an optical reading apparatus of the second embodiment.
Figures 9A, 9B, 9C:
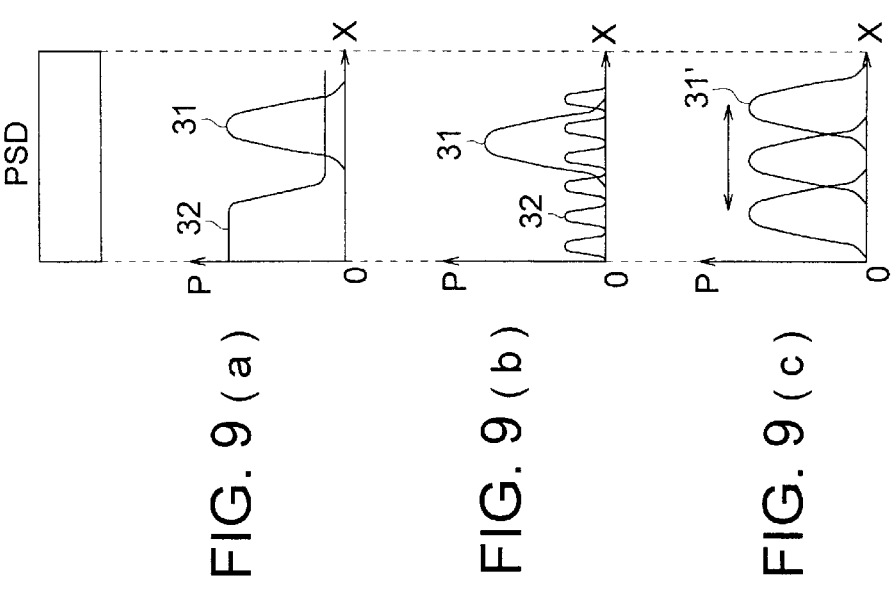

When paying attention only within the area received by the PSD as shown in FIG. 9(a) and FIG. 9(d), and the length of the PSD is defined as L, large quasi-signals are generated under the condition that the spatial frequency of the variation of reflecting rates of the subject is approximate to spatial frequency 1/L calculated from the PSD itself.

As shown in FIG. 9(b), FIG. 9(e) and FIG. 9(f), however, under either the condition that the period of reflected light 32 reflected from the background is less than the width equivalent to reflected light 31 of the essential linear light, or the condition that the distribution of reflecting rates gradually varies within the length L of the PSD, movement of the shift (ΔF), caused by the noise components of the centroid position calculated from the signals received and detected by the PSD, is small, and the disturbing degree of the quasi signals for the essential signals is also reduced.

Figure 10:
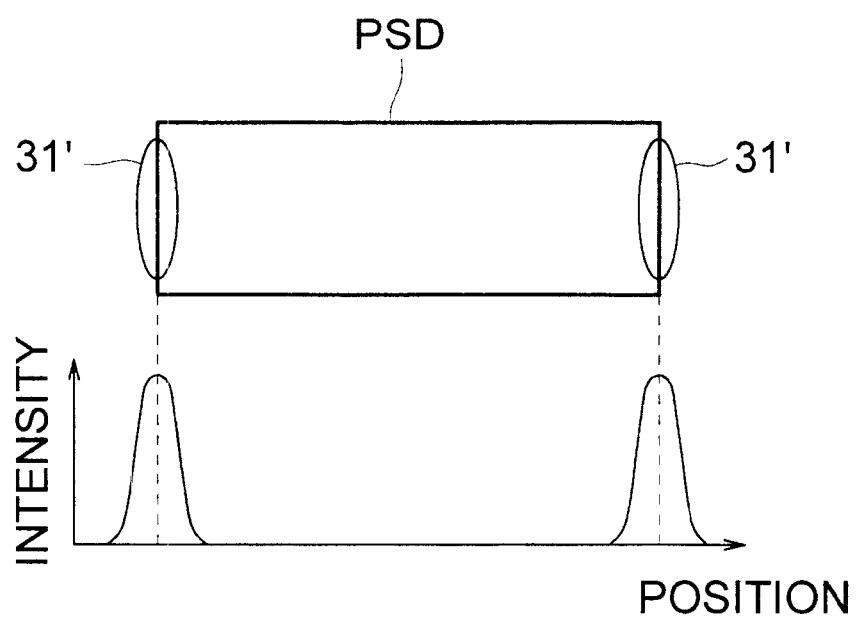
FIG. 10 shows an explanatory illustration indicating an operating mode of an optical reading apparatus of the second embodiment.

On the other hand, as shown in FIG. 9(c), when reflected light 31' is received only within the area being a sufficiently receivable by the PSD, the precise centroid of the light can be found from the calculating results of the output values of the PSD. However, when the reflected light is received at the end position of the PSD, as shown in FIG. 10, and the eclipse of the received light begins to occur, the calculating results of the output values of the PSD fall into disorder and generate a kind of quasi-signals. As a realistic countermeasure to overcome the abovementioned drawback, a moving range of the subject in both upper and lower directions (perpendicular direction to the surface of the subject) is limited so that the reflected light of the linear light does not enter the edge portions of the PSD, in order to prevent the above phenomenon.

As mentioned above, specifically, when the varying period of reflecting rate of the background of the subject is approximate to the spatial frequency of the length of 4, large quasi-signals caused by the distribution of reflecting rates are generated. In this case, the PSD is a kind of low-pass filter, and the distribution of reflecting rates (components of the quasi-signals calculated from the light outputted from all of the PSD) would belong to a low-frequency band.

From the abovementioned reasons, the output of the PSD can be regarded as a component synthesized into the abovementioned two frequency-bands (the quasi-signals in the low-frequency band, desired signals having a frequency other than the low-frequency band). Therefore, it becomes possible to obtain the information (the information of the deviations of at least one of the convex or the concave) of the subject, in which the influence of the quasi-signals is reduced, by reducing the noise components (the quasi-signals) caused by the optical mechanism by conducting the elimination calculating processing, as a separate arithmetic processing, before conducting the arithmetic processing.

Concretely speaking, according to the following procedures in the present embodiment, when detecting either the convex or the concave of subject 2, the signals relevant to the convex or the concave, being a detecting object with reduced noise components, was derived from the signals (the signals including the quasi-signals, serving as noise components) outputted from PSD 4 caused by the variation of reflecting rate generated by the information of the density contrast on the surface of subject 2.

At first, the two electronic current values I1, I2 outputted from the both ends of PSD 4 are converted to signal V1 and signal V2 through the processes of the I/V conversion, the amplifying operation and the A/D conversion, and then, signal V1 and signal V2, as time passage information, are stored in the memory during the moving action of subject 2.

In addition, signal P, which represents the centroid position of the light received on PSD 4, is also stored in the memory as time passage information as well. Signals P are derived from the equation of $$P=(V1-V2)/(V1+V2)$$

On the other hand, signal R, being a sum of signal V1 and signal V2, and derived from the equation of R =V1 +V2, is also stored in the memory in the passage of time as well.

In the above process, a plurality of signals employed for calculating each shift amount ΔF are quantities corresponding to the width of the illumination light emitted from the LD (the light source) onto subject 2 (width share (time share) of the light spot or the linear light of the illumination light in the moving direction of subject 2 at each reading timing).

By the use of each signal P and each shift amount ΔF obtained through the above process, and by subtracting the shift amount ΔF from the signal P at ever time of reading actions, each signal of the centroid position based on the convex or the concave, being a detecting object with reduced noise components, was found. This corresponds to the centroid position derived from signal I1' and signal I2', outputted from PSD 4, in which the noise components to be approximated at the essential position are reduced, based on the convex or the concave being a detecting object.

After each signal of the centroid position based on the convex or the concave, being a detecting object with reduced noise components, was found, the detecting operation of the convex or the concave, being a detecting object, was performed by using it, and characters and numerals expressed on the subject 2 were distinguished by means of the convex or the concave.

Figure 24:
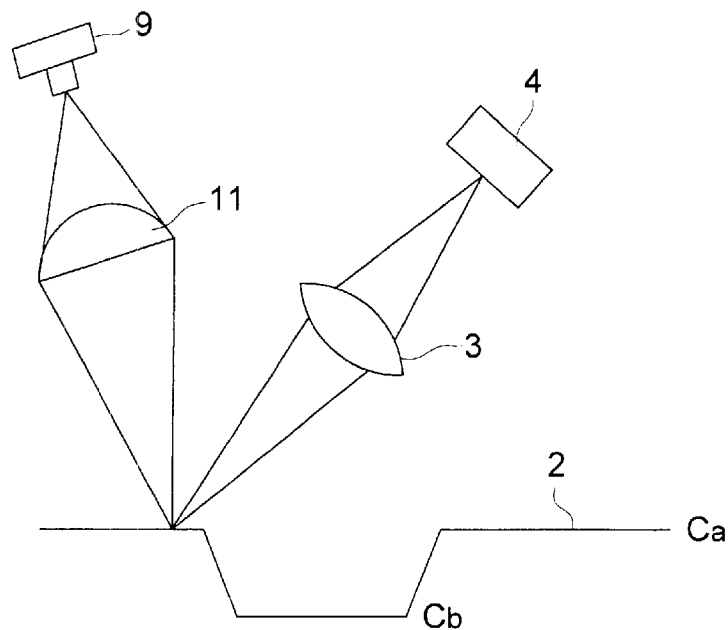
FIG. 24(a) and FIG. 24(b) show explanatory illustrations of an embodiment of the present invention, in which a PD array is employed for the photo-receiving element.
Figure 24:
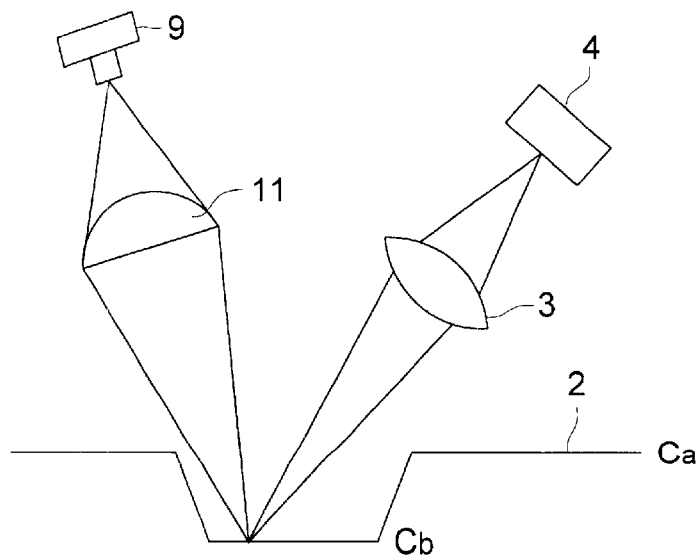
Figure 25:
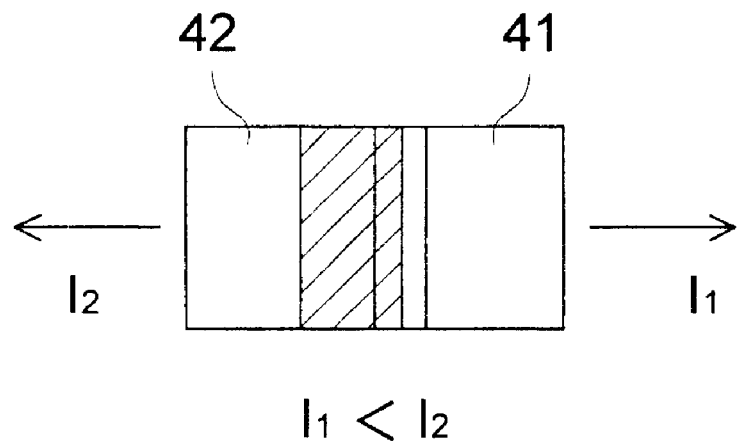
FIG. 25(a) and FIG. 25(b) show explanatory illustrations of a PD array.
Figure 25:
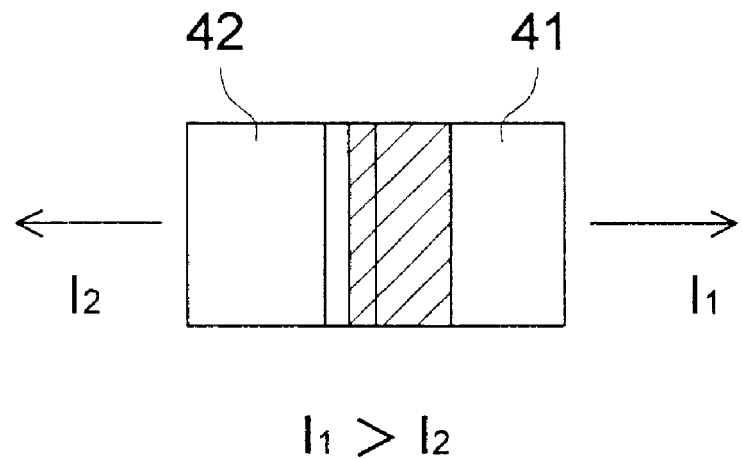

Next, referring to FIG. 24(a), FIG. 24(b), FIG. 25(a) and FIG. 25(b), an embodiment of the present invention, in which a PD array is employed for the photo-receiving element, will be detailed in the following. As shown in FIG. 25(a) and FIG. 25(b), in this embodiment, PD array 4 comprises PD 41 and PD 42 which are adjacent each other. Then, when the light is focused onto the area of level Ca as shown in FIG. 24(a), since an amount of the light irradiated onto PD 42 is larger than that irradiated onto PD 41 as shown in FIG. 25(a), electronic current $I_2$ generated by PD 42 is larger than electronic current $I_1$, generated by PD 41. On the other hand, when the light is focused onto the area of level Cb as shown in FIG. 24(b), since an amount of the light irradiated onto PD 41 is larger than that irradiated onto PD 42 as shown in FIG. 25(b), electronic current $I_1$, generated by PD 41 is larger than electronic current $I_2$ generated by PD 42.

Figure 26:
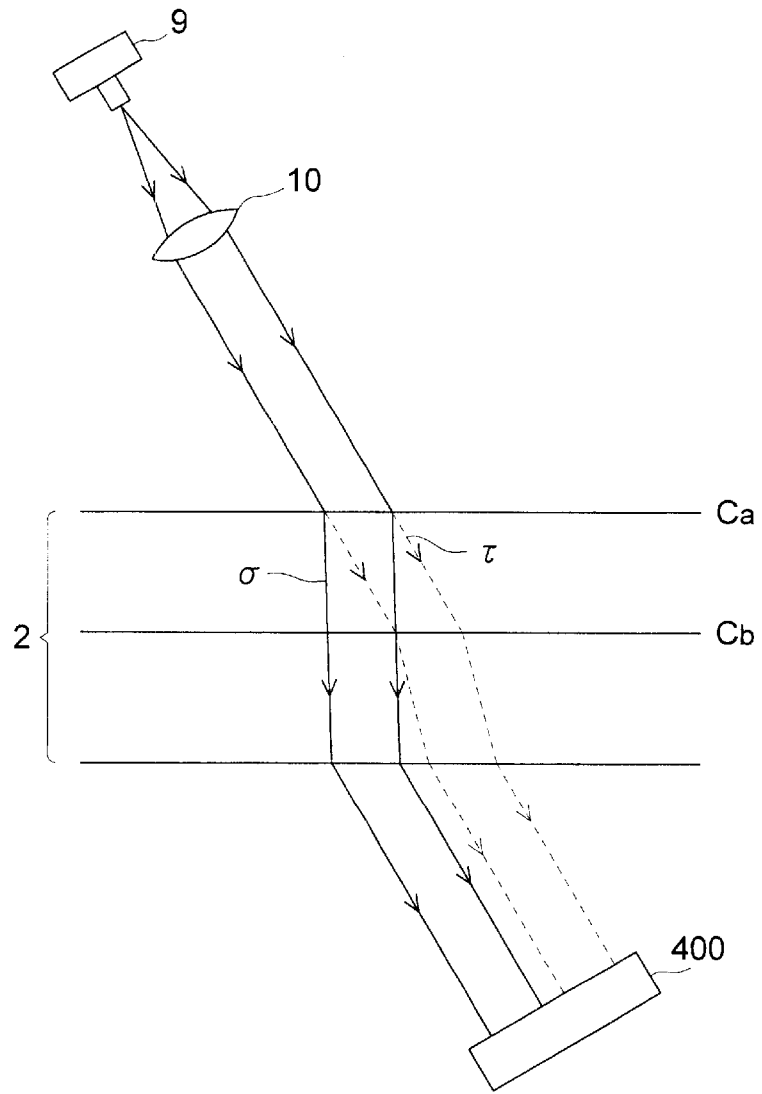
FIG. 26(a) and FIG. 26(b), show explanatory illustrations of an apparatus, embodied in the present invention, for obtaining information of the surface deviations of the subject by introducing the transmitted light penetrated through the subject.
Figure 26:
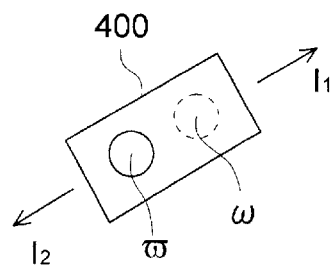

Next, referring to FIG. 26(a) and FIG. 26(b), an apparatus, embodied in the present invention, for obtaining information of the surface deviations of the subject by introducing the transmitted light penetrated through the subject to the photo-receiving element will be detailed in the following. As shown in FIG. 26(a), the apparatus comprises light source 9, collimator lens 10 for collimating the light flux emitted from light source 9 to irradiate subject 2, and PSD 400 for receiving the transmitted light penetrated through the subject.

When the surface of the subject resides at level Ca, the light flux emitted from light source 9 travels along the optical path indicated by solid line σ shown in FIG. 26(a), and enters into PSD 400. In this case, as shown in FIG. 26(b), since the light flux is projected onto position $\overline{\omega}$ of PSD 400, electronic current $I_2$ is larger than electronic current $I_1$. On the other hand, when the surface of the subject resides at level Cb, the light flux emitted from light source 9 travels along the optical path indicated by broken line τ shown in FIG. 26(a), and enters into PSD 400. In this case, as shown in FIG. 26(b), since the light flux is projected onto position ω of PSD 400, electronic current $I_1$, is larger than electronic current $I_2$. Accordingly, it becomes possible to detect the surface deviations of subject 2.

[Another Embodiment 1]

It is possible to employ the PSD having a two-dimensional photo-receiving surface or a solid-state imager having a two-dimensional photo-receiving surface (a CCD or a MOS imager) for the photo-receiving element in the abovementioned apparatus.

Even when the above photo-receiving element is employed, the outputs of the photo-receiving element in a time passage domain are in proportion to the distribution of reflecting rates of the subject, and it is possible to conduct the aforementioned subtracting operation based on the information of the outputs of the photo-receiving element stored within a short time. Therefore, it becomes possible to complete the arithmetic processing more quickly than in the method of finding the distribution after storing all of the information in the memory. Further, since the quantity of the information is large, it becomes possible to apply other various kinds of filters for the arithmetic processing. Still further, it becomes possible to conduct the detecting operation not only for the linear-type detecting object, but also for the two-dimensional detecting object at a time.

[Another Embodiment 2]

In the abovementioned apparatus, by employing a multi-segmented photo-diode for the photo-receiving element and by applying a method for detecting focus error signals of an optical pickup device, such as the knife edge method, the astigmatism method, the beam-size method or a combination of them, it is possible to detect the information caused by one of the convex or the concave on the surface of the subject.

Figure 11:
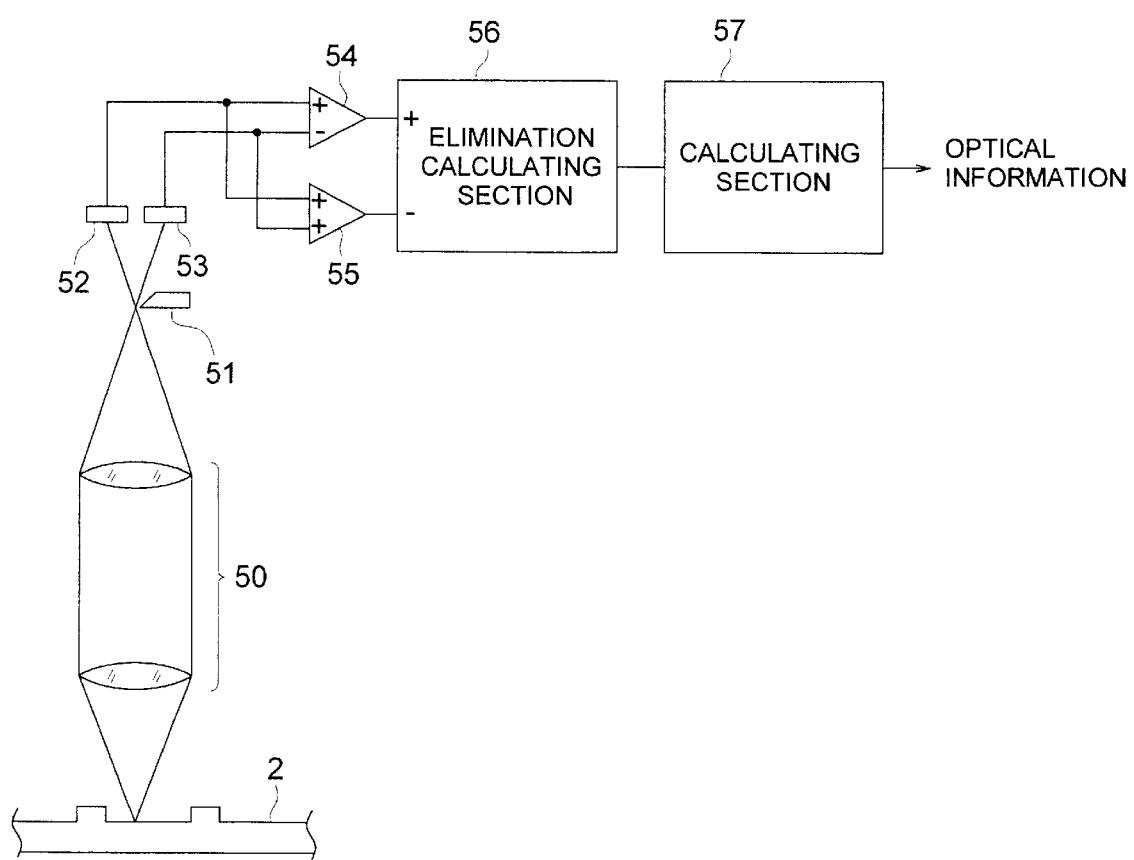
FIG. 11 shows a block diagram of an exemplified configuration of an optical reading apparatus of the second embodiment.

In ANOTHER EMBODIMENT 2 shown in FIG. 11, the laser beam emitted from the light source (not shown in the drawing) is focused onto subject 2, and optical system 50 collects the light diffused and reflected from subject 2 and guides the diffused and reflected light to first segment 52 and second segment 53 of the multi-segmented photo-diode, serving as a photo-receiving element. Then, subtracting circuit 54 generates the difference information between output values of first segment 52 and second segment 53 of the multi-segmented photo-diode. The information of at least one of the convex or the concave of subject 2 is detected by the relationship of the distance with subject 2. According to the configuration shown in FIG. 11, since knife-edge 51 is disposed in front of the multi-segmented photo-diode, and the balance of photo-receiving results of first segment 52 and second segment 53 of the multi-segmented photo-diode varies depending on at least one of the convex or the concave of subject 2, it is possible to detect at least one of the convex or the concave of subject 2.

However, when the distribution of reflecting rates caused by the density contrast resides on the surface of subject 2, the calculation result for the abovementioned difference information falls into disorder. Accordingly, giving an attention to the fact that the sum of the output values of first segment 52 and second segment 53 of the multi-segmented photo-diode is equivalent to the distribution of reflecting rates, it becomes possible to obtain the optical information in which the noise components caused by the optical factors are reduced, by generating the sum signals by means of adding circuit 55 and by subtracting the sum signals from the difference signals in elimination calculating section 56. Then, by the use of the signals in which the noise components caused by the optical factors are reduced, calculating section 57 detects the information caused by at least one of the convex or the concave of subject 2.

Incidentally, although the configuration of the knife-edge method is cited in the above descriptions, employing the known astigmatism method, the beam-size method, etc., as well, makes it possible to detect the optical information in the state that the noise components caused by the optical factors are reduced. Further, instead of any one of the knife-edge method, the astigmatism method and the beam-size method, a combination of the two or three methods is also applicable for this purpose.

[Another Embodiment 3]

Figure 12:
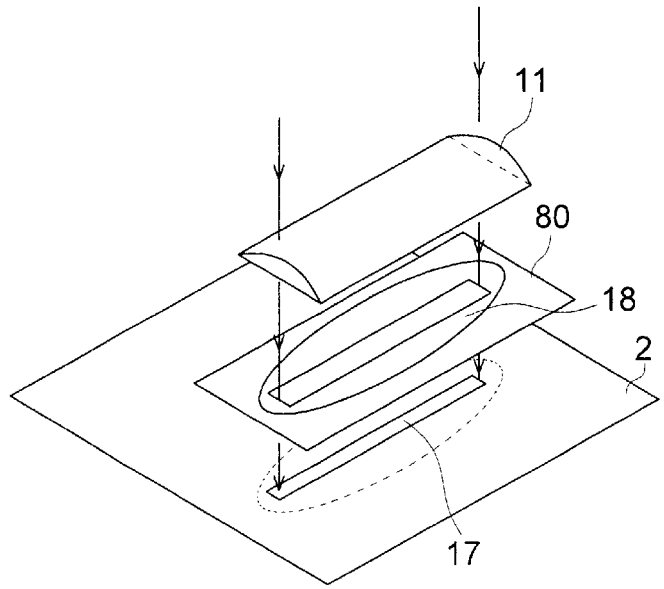
FIGS. 12(a)–12(c) show explanatory illustrations of an aperture member employed in another embodiment 3.
Figure 12:
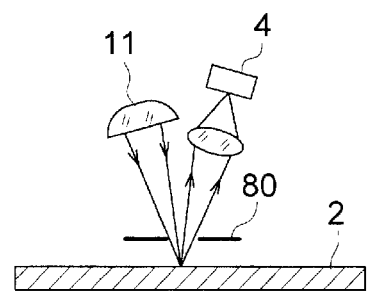
Figure 12:
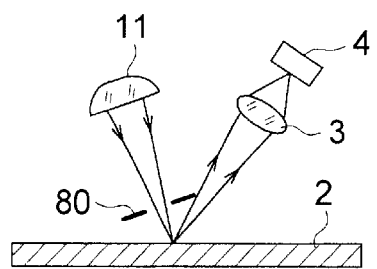

When an aperture member is disposed at a specific position in the reading optical system cited in each of the above embodiments, it becomes possible to further reduce the noise components. In other words, as shown in FIG. 12(a), when aperture 80, through which a portion of the light being equivalent to the liner light center area passes, while which shades a portion of the light being equivalent to the liner light diffusion area, is disposed at anywhere in the light path, it becomes possible to suppress the influence of the noise components caused by the optical factors. Incidentally, FIG. 12(b) shows an example of aperture 80, through which both the illumination light and the reflected light pass, while FIG. 12(c) shows another example of aperture 80, through which only the illumination light passes.

Specifically, when the photo-receiving area on the photo-receiving element is reduced by optimally disposing the aperture member, it is possible to reduce the low frequency noise components outputted in the time passage domain and which belong to the noise components caused by the optical factors.

As mentioned above, by adjusting the light entering into the photo-receiving element, it becomes possible to remove the noise components having frequencies lower than a predetermined frequency.

[Another Embodiment 4]

In the abovementioned apparatus, noise components, caused by the eclipsing actions of either the illumination light or the reflected light, which occur at an edge portion of at least one of the convex or the concave of the subject being a detecting object, can be cited as other noise components caused by the optical factors.

Figure 13:
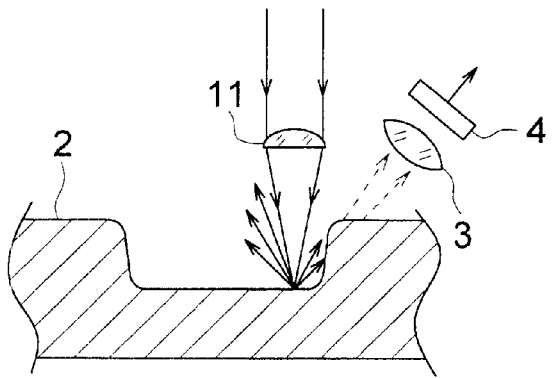
FIGS. 13(a)–13(c) show explanatory illustrations for explaining eclipsing actions in another embodiment 4.
Figure 13:
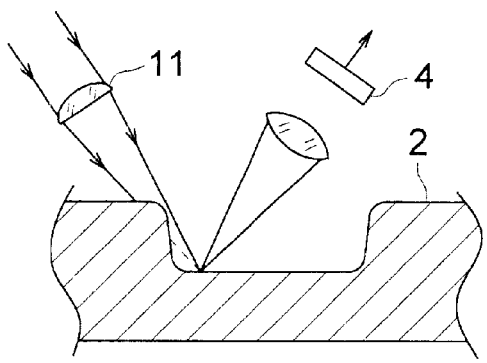
Figure 13:
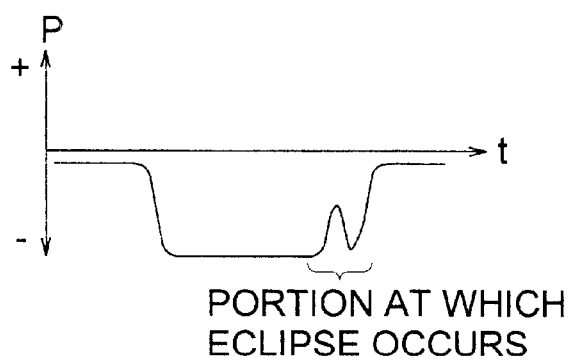

FIG. 13(a) shows a first detecting mode in which the illumination light enters onto subject 2 in a direction perpendicular to subject 2, while the reflected light is detected in a direction inclined to subject 2. FIG. 13(b) shows a second detecting mode in which the illumination light enters onto subject 2 in a direction inclined to subject 2, and the reflected light is detected in a direction inclined to subject 2. The eclipsing actions would possibly occur not only in both the first and second modes shown in FIG. 13(a) and FIG. 13(b), but also in another detecting mode in which the illumination light enters onto subject 2 in a direction inclined to subject 2, and the reflected light is detected in a direction perpendicular to subject 2 (not shown in the drawings). As shown in FIG. 13(c), the detecting result, obtained at the portion where the eclipsing actions occur, falls into disorder. Incidentally, the disorder mode of the read signal would vary depending on the position where the eclipsing actions occur.

To reduce the abovementioned disorder of the read signal, two illuminating optical systems or two receiving optical systems are disposed at symmetrical positions in respect to a surface perpendicular to the surface of the subject and the generated signals are synthesized or selected, for instance, to cancel the specific noise components.

Figure 14:
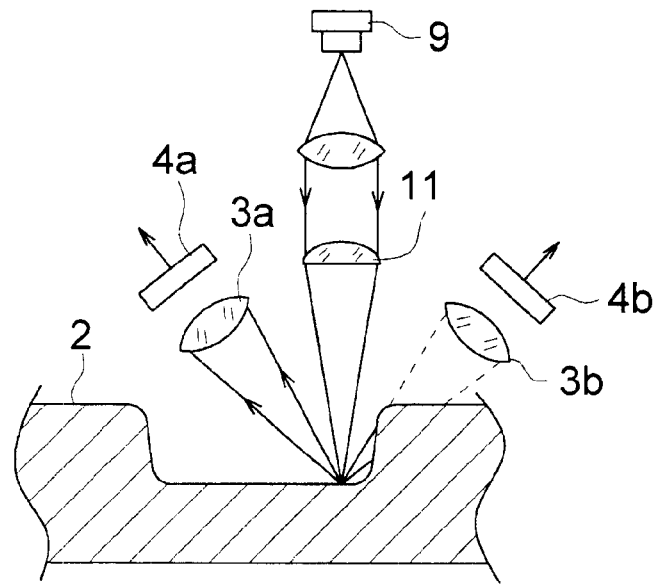
FIG. 14(a) and FIG. 14(b) show cross-sectional views of an exemplified configuration of an optical reading apparatus of another embodiment 4.
Figure 14:
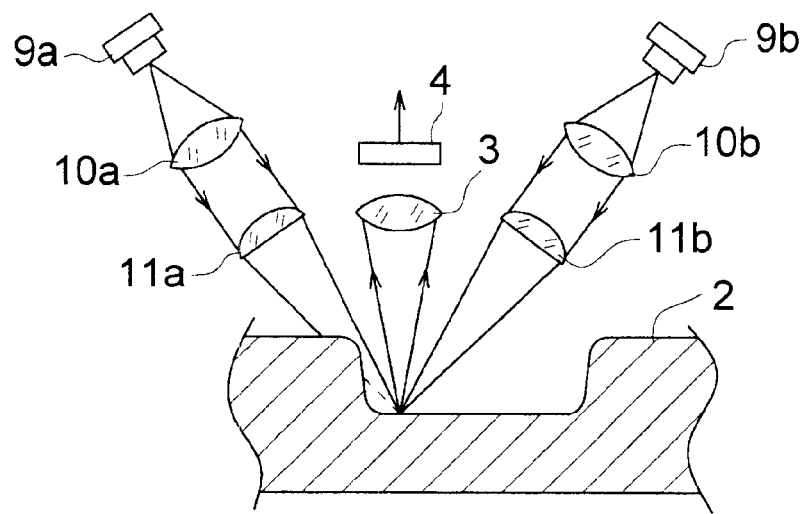

For instance, as shown in FIG. 14(a), both PSD 4a and PSD 4b are disposed in inclined directions at both sides in respect to the illuminating light entering from a perpendicular direction, and the signals outputted from either PSD 4a or PSD 4b are selected to utilize the signals, having no disorder caused by the eclipsing actions, for the arithmetic processing. In the above embodiment, a plurality of photo-receiving elements are symmetrically disposed, and the photo-receiving results of the plurality of photo-receiving elements are synthesized or selected to reduce the noise components caused by the optical factors, and as a result, the influence of the noise components is suppressed. Further, as shown in FIG. 14(c), it is also applicable that both LD 9a and LD 9b are disposed in inclined directions at both sides, and PSD 4 detects the light reflected in a perpendicular direction at the center. In the above embodiment, a plurality of light sources are symmetrically disposed to cancel the noise components caused by the optical factors with each of the light, and as a result, the influence of the noise components is suppressed.

As detailed in the above, according to the present invention, in an optical reading method or an optical reading apparatus, in which objective information are obtained by optically reading the subject, and then, applying an arithmetic processing to the read results, it becomes possible to reduce the influence of the noise components caused by the optical factors and to improve the accuracy of the necessary information being a detecting object.

Disclosed embodiment can be varied by a skilled person without departing from the spirit and scope of the invention.

What is claimed is:

1. An apparatus for optically reading information residing on a subject which has a reference plane, said information being formed by at least one of a convex area protruded from said reference plane and a concave area caved into said reference plane, said apparatus comprising:

a light source to irradiate a light flux onto said subject;

a photo-receiving element to receive either a reflected light or a transmitted light coming from said subject when said light flux is irradiated onto said subject, wherein said photo-receiving element is capable of detecting a photo-receiving position so as to generate original signals in response to variations of said photo-receiving position through a photoelectronic conversion process, and said original signals include informational signals representing said information and a noise component caused by either reflectance variations or transmittance variations distributing over said subject; and a noise-elimination calculating section to reduce said noise component included in said original signals by applying a noise-elimination calculating operation to said original signals, so as to output processed signals in which a level of said noise component is reduced lower than that included in said original signals, wherein said noise-elimination calculating operation includes the steps of:

finding a first centroid of light totally projected onto said photo-receiving element, from said original signals generated by said photo-receiving element;

finding a second centroid of light caused by either said reflectance variations or said transmittance variations distributing over said subject, from said original signals generated by said photo-receiving element; and obtaining said processed signals by subtracting said second centroid of light from said first centroid of light in said original signals.

2. The apparatus of claim 1, further comprising:

an arithmetic processing section to apply an arithmetic processing to said processed signals, so as to detect said information residing on said subject.

3. The apparatus of claim 1, wherein said noise-elimination calculating section finds said second centroid of light from a total amount of light projected onto said photo-receiving element.

4. The apparatus of claim 3, wherein said photo-receiving element is a one-dimensional PSD (Position Sensitive Detector), including a first end port and a second end port, which are located at both ends of said one-dimensional PSD; and wherein said noise-elimination calculating section finds said first centroid of light from a first electrical value outputted from said first end port and a second electrical value outputted from said second end port, while said noise-elimination calculating section finds said second centroid of light from a sum of said first electrical value and said second electrical value.

5. The apparatus of claim 4, wherein said noise-elimination calculating section comprises a memory to store said first electrical value, said second electrical value and said sum of them; and wherein said noise-elimination calculating section finds said first centroid of light from said first electrical value and said second electrical value, both of which are stored in said memory in advance, while said noise-elimination calculating section finds said second centroid of light from said sum stored in said memory in advance.

6. The optical reading apparatus of claim 4, wherein said light flux is irradiated onto said subject while said subject is moving relative to said light flux, having a width in a moving direction of said subject or said light flux; and wherein a light-spot width of light projected onto said photo-receiving element corresponds to said width of said light flux, and said noise-elimination calculating section finds said second centroid of light in respect to said light-spot width from a sum of said first electrical value and said second electrical value.

7. The apparatus of claim 4, wherein said first electrical value and said second electrical value are either two electric current values or two electric voltage values outputted from said both ends of said one-dimensional PSD.

8. The apparatus of claim 1, wherein said light flux is irradiated onto said subject while said subject is moving relative to said light flux in a moving direction, and said light flux is a linear light being slender in a direction orthogonal to said moving direction.

9. The apparatus of claim 1, wherein said noise-elimination calculating section finds said noise component, based on a difference between frequency components of said original signals generated by said photo-receiving element.

10. The apparatus of claim 1, wherein said photo-receiving element is either a PSD (Position Sensitive Detector), a PD (Photo Diode) or a solid-state imager.

11. The apparatus of claim 1, wherein said photo-receiving element is a multi-segmented photo-diode, and wherein one of a knife edge method, an astigmatism method and a beam-size method is employed for detecting at least one of said convex area protruded from said reference plane and said concave area caved into said reference plane.

12. The apparatus of claim 1, further comprising:

an aperture to optically shade said noise component caused by either said reflectance variations or said transmittance variations distributing over said subject.

13. The apparatus of claim 1, wherein a plurality of light sources, each of which is equivalent to said light source, are symmetrically disposed, so as to optically reduce said noise component caused by either said reflectance variations or said transmittance variations distributing over said subject.

14. The apparatus of claim 1, wherein a plurality of photo-receiving elements, each of which is equivalent to said photo-receiving element, are symmetrically disposed, and wherein photo-receiving results outputted from said photo-receiving elements are synthesized or selected, so as to optically reduce said noise component caused by either said reflectance variations or said transmittance variations distributing over said subject.

15. A method for optically reading information residing on a subject which has a reference plane, said information being formed by at least one of a convex area protruded from said reference plane and a concave area caved into said reference plane, comprising the steps of:

irradiating a light flux emitted from light source onto said subject;

receiving either a reflected light or a transmitted light coming from said subject with a photo-receiving element, which is capable of detecting a photo-receiving position;

generating original signals in response to variations of said photo-receiving position through a photoelectronic conversion process, said original signals including informational signals representing said information and a noise component caused by either reflectance variations or transmittance variations distributing over said subject; and applying a noise-elimination calculating operation to said original signals, so as to reduce said noise component included in said original signals and to output processed signals in which a level of said noise component is reduced lower than that included in said original signals, wherein said noise-elimination calculating operation includes the steps of: finding a first centroid of light totally projected onto said photo-receiving element, from said original signals generated by said photo-receiving element;

finding a second centroid of light caused by either said reflectance variations or said transmittance variations distributing over said subject, from said original signals generated by said photo-receiving element; and obtaining said processed signals by subtracting said second centroid of light from said first centroid of light In said original signals.

16. The method of claim 15, further comprising the step of:

applying an arithmetic processing to said processed signals, so as to detect said information residing on said subject.

17. The method of claim 15, wherein, in said noise-elimination calculating operation, said second centroid of light is found from a total amount of light projected onto said photo-receiving element.

* * * * *